United States Patent [19]

Küber et al.

[11] Patent Number: 5,770,753
[45] Date of Patent: Jun. 23, 1998

[54] METALLOCENES CONTAINING ARYL-SUBSTITUTED INDENYL DERIVATIVES AS LIGANDS, PROCESS FOR THEIR PREPARATION, AND THEIR USE AS CATALYSTS

[75] Inventors: Frank Küber, Oberursel; Bernd Bachmann, Eppstein/Taunus; Walter Spaleck, Liederbach/Taunus; Andreas Winter, Glashütten/Taunus; Jürgen Rohrmann, Kelkheim, all of Germany

[73] Assignee: Targor GmbH, Germany

[21] Appl. No.: 475,155

[22] Filed: Jun. 7, 1995

Related U.S. Application Data

[62] Division of Ser. No. 83,816, Jun. 28, 1993, abandoned.

[30] Foreign Application Priority Data

Jun. 27, 1992 [DE] Germany ............... 4221244.8

[51] Int. Cl.$^6$ ................................ C08F 4/642
[52] U.S. Cl. ................. 556/11; 556/53; 556/43; 556/58; 556/28; 556/22; 556/23; 502/103; 502/117; 526/943; 526/160; 526/127
[58] Field of Search ................. 556/11, 43, 53, 556/58; 502/103, 117

[56] References Cited

U.S. PATENT DOCUMENTS

| | | | |
|---|---|---|---|
| 4,769,510 | 9/1988 | Kaminsky et al. | 585/512 |
| 5,017,714 | 5/1991 | Welborn, Jr. | 556/12 |
| 5,145,819 | 9/1992 | Winter et al. | 502/117 |
| 5,278,264 | 1/1994 | Spaleck et al. | 576/127 |
| 5,296,434 | 3/1994 | Karl et al. | 502/117 |
| 5,304,614 | 4/1994 | Winter et al. | 526/127 |
| 5,328,969 | 7/1994 | Winter et al. | 526/127 |
| 5,329,033 | 7/1994 | Spaleck et al. | 556/53 |
| 5,374,752 | 12/1994 | Winter et al. | 556/11 |
| 5,561,093 | 10/1996 | Fujita et al. | 502/117 |
| 5,616,663 | 4/1997 | Imuta et al. | 526/127 |
| 5,629,254 | 5/1997 | Fukuoka et al. | 502/117 |
| 5,658,997 | 8/1997 | Fukuoka et al. | 526/127 |

FOREIGN PATENT DOCUMENTS

| | | | |
|---|---|---|---|
| A-21254/92 | 3/1993 | Australia | C08F 4/64 |
| 2055216 | 5/1992 | Canada | C08F 2/00 |
| 2055218 | 5/1992 | Canada | C07F 7/00 |
| 1317411 | 5/1993 | Canada | C08F 2/04 |
| 0 442 725 A2 | 8/1991 | European Pat. Off. | C08F 10/00 |
| 0 529 908 A1 | 3/1993 | European Pat. Off. | C08F 10/00 |

OTHER PUBLICATIONS

W. Kaminsky, et al. (1985) Angew. Chem. Int'l. Ed., Engl. 24, 507–8.
*Hawley's Condensed Chemical Dictionary,* 11th Ed., Von-Nostrand–Reinhold, New York (1987), inside front cover.

Ewen et al, "Crystal Structures and Stereospecific Propylene Polymerizations with Chiral Hafnium Metallocene Catalysts," J. Am. Chem. Soc. (1987), vol. 109, pp. 6544–6545.

*Primary Examiner*—Mark Nagumo
*Attorney, Agent, or Firm*—Connolly & Hutz

[57] ABSTRACT

Metallocenes containing aryl-substituted indenyl derivatives as ligands, process for their preparation, and their use as catalysts.

A very effective catalyst system for the polymerization or copolymerization of olefins comprises a cocatalyst, preferably an aluminoxane or a supported aluminoxane, and a metallocene of the formula I

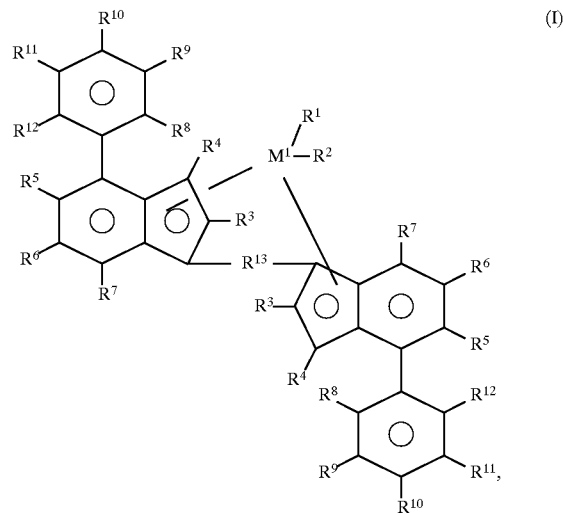

in which, in the preferred form, $M^1$ is Zr or Hf, $R^1$ and $R^2$ are halogen or alkyl, $R^3$ is alkyl, $R^4$ to $R^{12}$ are alkyl or hydrogen and $R^{13}$ is a (substituted) alkylene or heteroatom bridge.

The metallocenes, in particular the zirconocenes, produce polymers of very high molecular weight, in the case of prochiral monomers polymers of very high molecular weight, very high stereotacticity and very high melting point, at high catalyst activities in the industrially particularly interesting temperature range between 50° and 80° C. In addition, reactor deposits are avoided by means of supported catalyst systems.

5 Claims, No Drawings

METALLOCENES CONTAINING ARYL-SUBSTITUTED INDENYL DERIVATIVES AS LIGANDS, PROCESS FOR THEIR PREPARATION, AND THEIR USE AS CATALYSTS

This is a divisional of application Ser. No. 08/083,816 filed on Jun. 28, 1993 abandoned.

Metallocenes containing aryl-substituted indenyl derivatives as ligands, process for their preparation, and their use as catalysts.

The invention relates to novel metallocenes containing aryl-substituted indenyl derivatives as ligands which can be used very advantageously as catalysts components in the preparation of polyolefins of high isotacticity, narrow molecular-weight distribution and very high molecular weight.

Polyolefins of high molecular weight are of particular importance for the production of films, sheets or large hollow articles or moldings, such as, for example, pipes.

The literature discloses the preparation of polyolefins using soluble metallocene compounds in combination with aluminoxanes or other cocatalysts which, due to their Lewis acidity, are able to convert the neutral metallocene into a cation and stabilize it.

Soluble metallocene compounds based on bis(cyclopentadienyl) dialkylzirconium or bis(cyclopentadienyl) zirconium dihalide in combination with oligomeric aluminoxanes are capable of polymerizing ethylene in good activity and propylene in moderate activity. Polyethylene having a narrow molecular-weight distribution and moderate molecular weight is obtained. The polypropylene prepared in this way is atactic and has a very low molecular weight.

The preparation of isotactic polypropylene is achieved with the aid of ethylenebis (4,5,6,7-tetrahydro-1-indenyl) zirconium dichloride together with an aluminoxane in a suspension polymerization (cf. EP 185 918). The polymer has a narrow molecular-weight distribution. A particular disadvantage of this process is that, at industrially relevant polymerization temperatures, only polymers having a very low molecular weight can be prepared.

A special preactivation method for the metallocene using an aluminoxane has also been proposed, resulting in a significant increase in the activity of the catalyst system and in a considerable improvement in the grain morphology of the polymer (cf. DE 37 26 067). However, the preactivation hardly increases the molecular weight at all.

Also known are catalysts based on ethylenebisindenylhafnium dichloride and ethylenebis (4,5,6,7-tetrahydro-1-indenyl) hafnium dichloride and methylaluminoxane, by means of which relatively high-molecular-weight polypropylenes can be prepared by suspension polymerization (cf. J. Am. Chem. Soc. (1987), 109, 6544). However, the grain morphology of the polymers produced in this way under industrially relevant polymerization conditions is unsatisfactory, and the activity of the catalyst systems employed is comparatively low. Together with the high catalysts costs, inexpensive polymerization using these systems is thus impossible.

A significant increase in the molecular weight has been achieved by using metallocenes in which the aromatic π-ligands fixed by a bridge carry substituents in the 2-position (cf. DE 40 35 886) or in the 2- and 4-position (cf. DE 41 28 238).

A further increase in the molecular weight has been achieved by using aromatic π-ligands containing substituents in the 2-, 4- and 6-position (cf. DE 41 39 596) and aromatic π-ligands of the 4,5-benzoindenyl type (cf. DE 41 39 595).

The last-mentioned metallocenes containing said substituents are already very effective in this respect at the polymerization temperature of 70° C. Nevertheless, the molecular weights which can be achieved at the industrially optimum polymerization temperature of 70° C. are still too low for many industrial applications, such as, for example, the preparation of polymers for pipes and large hollow articles, and in particular fibers.

Under the constraints of inexpensive large-scale production, polymerizations must be carried out at the highest possible reaction temperature, since the heat of reaction produced at relatively high polymerization temperatures can be dissipated using little cooling medium. The cooling-water circuit can therefore be made significantly smaller.

A disadvantage which frequently occurs in soluble (homogeneous) metallocene/methylaluminoxane catalyst systems in processes in which the polymer is formed as a solid is the formation of thick deposits on reactor walls and stirrer. These deposits are formed by agglomeration of the polymer particles if the metallocene, or aluminoxane, or both, are in the form of a solution in the suspension medium. Deposits of this type in the reactor systems must be removed regularly, since they rapidly achieve considerable thicknesses, have high strength and hinder heat exchange with the cooling medium.

It is therefore advantageous to employ metallocenes in supported form. An efficient and simple process for supporting metallocenes which can be employed universally in all polymerization processes has been proposed (cf. EP 92 107331.8).

A further disadvantage in the case of stereospecific polymerization of prochiral monomers, for example of propylene, using metallocene catalysts is the relatively low isotacticity, which results in low melting points in the case of isotactic polypropylene. In particular metallocenes containing substituents in the 2- and 4-position and specifically rac-dimethyl-silylbis (2-methyl-4-isopropylindenyl) zirconium dichloride in combination with methylaluminoxane gives, in the case of propylene, a polymer of high isotacticity and thus high melting point (cf. DE 41 28 238). Nevertheless, the melting points which can be achieved are too low at industrially relevant polymerization temperatures (for example 70° C.) for some industrial applications.

However, there are also industrial applications in which low melting points are desired.

The object was to find a process and/or a catalyst system which produces polymers of very high molecular weight and, in the case of isospecific polymerization of prochiral monomers, polymers of high isotacticity in high yield. The use of a support would prevent the disadvantages known from the prior art caused by deposit formation and a high proportion of fine particles. The use of hydrogen as molecular weight regulator should then enable the entire range of industrially interesting molecular weights to be covered by means of only a single metallocene.

It has been found that metallocenes containing specific indenyl derivatives as ligands are suitable catalysts (catalyst components) in the preparation of polyolefins of high molecular weight, in particular on use of prochiral monomers of isotactic polyolefins of very high molecular weight and very high isotacticity.

Reaction of these soluble metallocenes with a supported organoaluminum catalyst component gives a catalyst system which requires no additional cocatalyst for activation and completely prevents formation of reactor deposits.

The present invention therefore relates to compounds of the formula I:

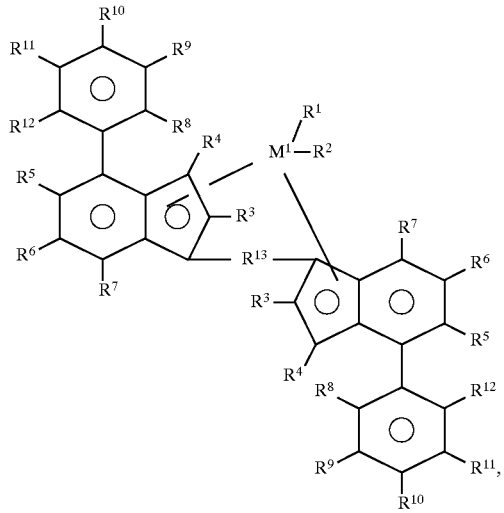

in which
M$^1$ is a metal from group IVb of the Periodic Table,
R$^1$ and R$^2$ are identical or different and are a hydrogen atom, a C$_1$–C$_{10}$-alkyl group, a C$_1$–C$_{10}$-alkoxy group, a C$_6$–C$_{10}$-aryl group, a C$_6$–C$_{10}$-aryloxy group, a C$_2$–C$_{10}$-alkenyl group, a C$_7$–C$_{40}$-arylalkyl group, a C$_7$–C$_{40}$-alkylaryl group, a C$_8$–C$_{40}$-arylalkenyl group, an OH group or a halogen atom, the radicals R$^3$ are identical or different and are a hydrogen atom, a halogen atom, a C$_1$–C$_{10}$-alkyl group, which may be halogenated, a C$_6$–C$_{10}$-aryl group, an —NR$^{16}{}_2$, —SR$^{16}$, —OSiR$^{16}{}_3$, —SiR$^{16}{}_3$ or —PR$^{16}{}_2$ radical, in which R$^{16}$ is a halogen atom, a C$_1$–C$_{10}$-alkyl group or a C$_6$–C$_{10}$-aryl group, R$^4$ to R$^{12}$ are identical or different and are as defined for R$^3$, or adjacent radicals R$^4$ to R$^{12}$, together with the atoms connecting them, form one or more aromatic or aliphatic rings, or the radicals R$^5$ and R$^8$ or R$^{12}$, together with the atoms connecting them, form an aromatic or aliphatic ring,
R$^{13}$ is

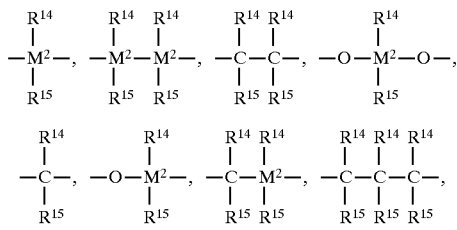

=BR$^{14}$, =AlR$^{14}$, —Ge—, —O—, —S—, =SO, =SO$_2$, =NR$^{14}$, =CO, =PR$^{14}$ or =P(O)R$^{14}$, where R$^{14}$ and R$^{15}$ are identical or different and are a hydrogen atom, a halogen atom, a C$_1$–C$_{10}$-alkyl group, a C$_1$–C$_{10}$-fluoroalkyl group, a C$_1$–C$_{10}$-alkoxy group, a C$_6$–C$_{10}$-aryl group, a C$_6$–C$_{10}$-fluoroaryl group, a C$_6$–C$_{10}$-aryloxy group, a C$_2$–C$_{10}$-alkenyl group, a C$_7$–C$_{40}$-arylalkyl group, a C$_7$–C$_{40}$-alkylaryl group or a C$_8$–C$_{40}$-arylalkenyl group, or R$^{14}$ and R$^{15}$, in each case together with atoms connecting them, form one or more rings, and M$^2$ is silicon, germanium or tin.

The present invention also relates to a process for the preparation of an olefin polymer by polymerization or copolymerization of an olefin of the formula R$^a$—CH═CH—R$^b$, in which R$^a$ and R$^b$ are identical or different and are a hydrogen atom or a hydrocarbon radical having 1 to 14 carbon atoms, or R$^a$ and R$^b$, together with the atoms connecting them, may form one or more rings, at a temperature of from −60° to 200° C., at a pressure from 0.5 to 100 bar, in solution, in suspension or in the gas phase, in the presence of a catalyst formed from a metallocene as transition-metal compound and a cocatalyst, wherein the metallocene is a compound of the formula I.

The compounds according to the invention are metallocenes of the formula I

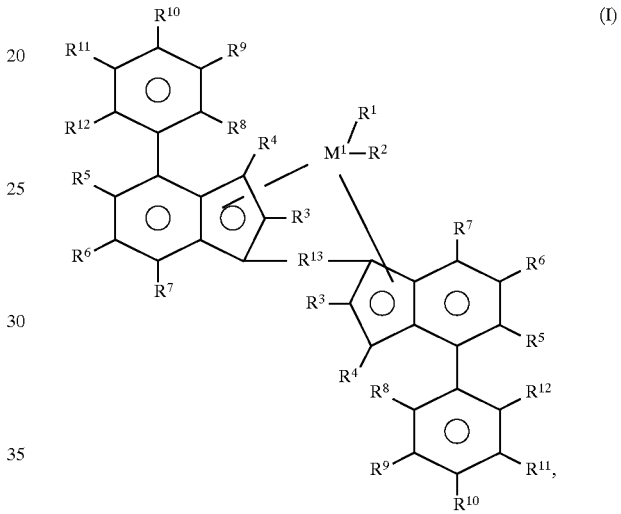

in which M$^1$ is a metal from group IVb of the Periodic Table, for example titanium, zirconium, hafnium, vanadium, niobium, tantalum, chromium, molybdenum or tungsten, preferably zirconium, hafnium or titanium.

R$^1$ and R$^2$ are identical or different and are a hydrogen atom, a C$_1$–C$_{10}$-, preferably C$_1$–C$_3$-alkyl group, a C$_1$–C$_{10}$-, preferably C$_1$–C$_3$-alkoxy group, a C$_6$–C$_{10}$-, preferably C$_6$–C$_8$-aryl group, a C$_6$–C$_{10}$-, preferably C$_6$–C$_8$-aryloxy group, a C$_2$–C$_{10}$-, preferably C$_2$–C$_4$-alkenyl group, a C$_7$–C$_{40}$-, preferably C$_7$–C$_{10}$-arylalkyl group, a C$_7$–C$_{40}$-, preferably C$_7$–C$_{12}$-alkylaryl group, a C$_8$–C$_{40}$-, preferably C$_8$–C$_{12}$-arylalkenyl group, or a halogen atom, preferably chlorine.

The radicals R$^3$ to R$^{12}$ are identical or different and are a hydrogen atom, a halogen atom, preferably fluorine, chlorine or bromine, a C$_1$–C$_{10}$-, preferably C$_1$–C$_4$-alkyl group, which may be halogenated, a C$_6$–C$_{10}$-, preferably C$_6$–C$_8$-aryl group, an —NR$^{16}{}_2$, —SR$^{16}$, —OSiR$^{16}{}_3$, —SiR$^{16}{}_3$ or —PR$^{16}{}_2$ radical, where R$^{16}$ can be a halogen atom, preferably chlorine, or a C$_1$–C$_{10}$-, preferably C$_1$–C$_4$-alkyl group or a C$_6$–C$_{10}$-, preferably C$_6$–C$_8$-aryl group.

The adjacent radicals R$^4$ to R$^{12}$, together with the atoms connecting them, can form an aromatic, preferably 6-membered aromatic or aliphatic, preferably 4–8-membered aliphatic ring.

$R^{13}$ is

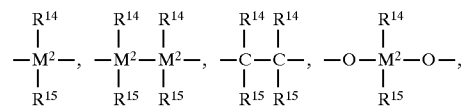

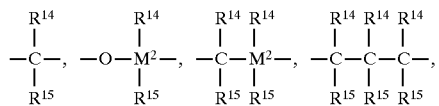

$=BR^{14}$, $=AlR^{14}$, $-Ge-$, $-O-$, $-S-$, $=SO$, $=SO_2$, $=NR^{14}$, $=CO$, $=PR^{14}$ or $=P(O)R^{14}$, preferably

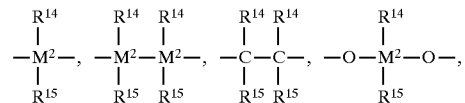

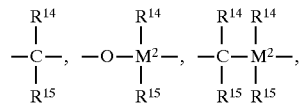

$=BR^{14}$, $=AlR^{14}$, $-Ge-$, $-O-$, $-S-$, $=SO$, $=SO_2$, $=NR^{14}$, $=CO$, $=PR^{14}$ or $=P(O)R^{14}$, where $R^{14}$ and $R^{15}$ are identical or different and are a hydrogen atom, a halogen atom, a $C_1-C_{10}-$, preferably a $C_1-C_4$-alkyl group, in particular a methyl group, a $C_1-C_{10}$-fluoroalkyl group, preferably a $CF_3$ group, a $C_6-C_{10}-$, preferably $C_6-C_8$-aryl group, a $C_6-C_{10}-$ fluoroaryl group, preferably a pentafluorophenyl group, a $C_1-C_{10}-$, preferably $C_1-C_4$-alkoxy group, in particular a methoxy group, a $C_2-C_{10}-$, preferably $C_2-C_4$-alkenyl group, a $C_7-C_{40}-$, preferably $C_7-C_{10}$-arylalkyl group, a $C_8-C_{40}-$, preferably $C_8-C_{12}$-arylalkenyl group, a $C_7-C_{40}-$, preferably $C_7-C_{12}$-alkylaryl group, or $R^{14}$ and $R^{15}$, in each case with the atoms connecting them, form a ring.

$M^2$ is silicon, germanium or tin, preferably silicon or germanium.

For compounds of the formula I, it is preferred that $M^1$ is zirconium or hafnium, $R^1$ and $R^2$ are identical and are a $C_1-C_3$-alkyl group or a halogen atom, the radicals $R^3$ are identical and are a $C_1-C_4$-alkyl group, $R^4$ to $R^{12}$ are identical or different and are hydrogen or a $C_1-C_4$-alkyl group, $R^{13}$ is

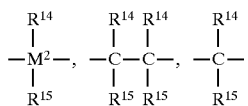

where $M^2$ is silicon or germanium and $R^{14}$ and $R^{15}$ are identical or different and a $C_1-C_4$-alkyl group or a $C_6-C_{10}$-aryl group.

Preference is furthermore given to the compounds of formula I in which the radicals $R^4$ and $R^7$ are hydrogen, and $R^5$, $R^6$ and $R^8$ to $R^{12}$ are a $C_1-C_4$-alkyl group or hydrogen.

Particular preference is given to compounds of the formula I in which $M^1$ is zirconium, $R^1$ and $R^2$ are identical and are chlorine, the radicals $R^3$ are identical and are a $C_1-C_4$-alkyl group, $R^4$ and $R^7$ are hydrogen, $R^5$, $R^6$ and $R^8$ to $R^{12}$ are identical or different and are a $C_1-C_4$-alkyl group or hydrogen, and $R^{13}$ is

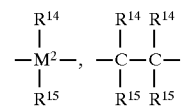

where $M^2$ is silicon, and $R^{14}$ and $R^{15}$ are identical or different and are a $C_1-C_4$-alkyl group or a $C_6-C_{10}$-aryl group.

The preparation of the metallocene I is carried out by processes known from the literature and is shown in the reaction scheme below:

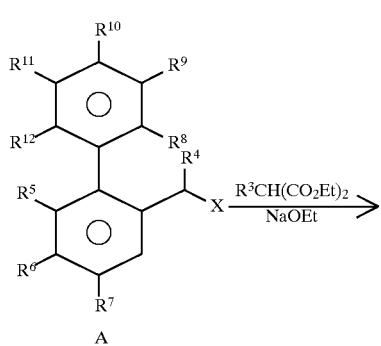

A

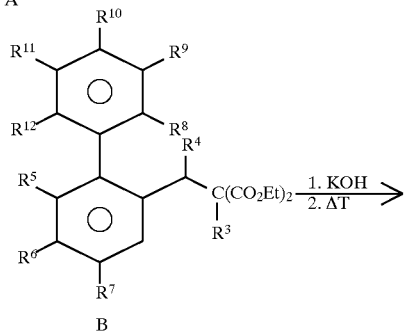

B

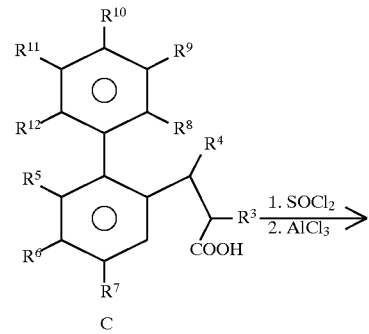

C

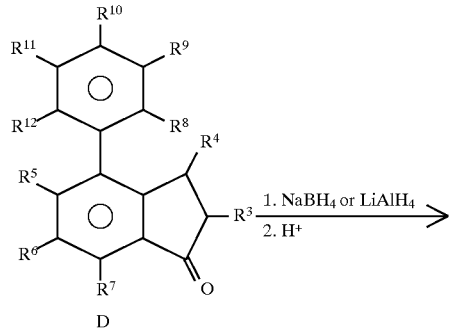

D

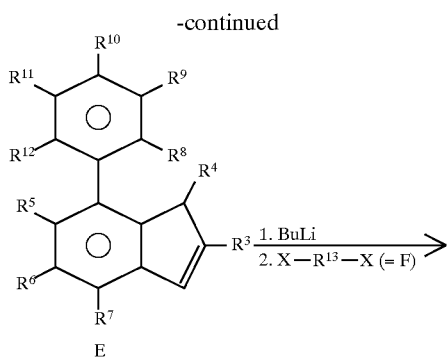

X = a nucleophilic leaving group, for example halogen or tosyl.

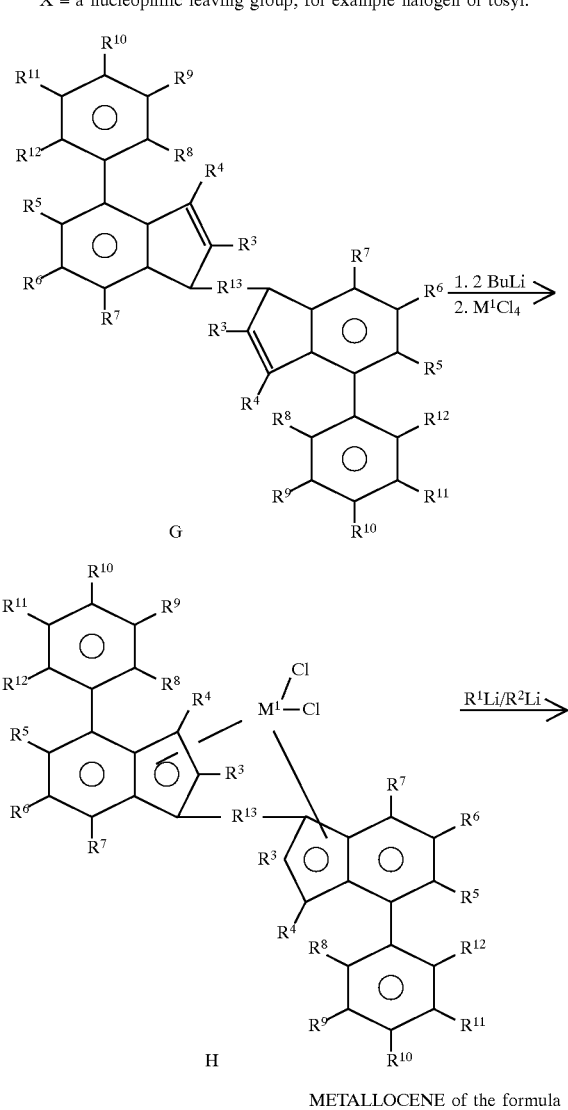

METALLOCENE of the formula I

The 2-phenylbenzyl halide derivatives of the formula A are commercially available or can be prepared by methods known from the literature.

The conversion to the compounds of the formula B is carried out by reaction with substituted malonic esters under basic conditions, such as, for example, in ethanolic solutions of sodium ethoxide.

The compounds of the formula B are hydrolyzed by means of alkali metal hydroxides, such as potassium hydroxide or sodium hydroxide, and the resultant dicarboxy-lic acids are decarboxylated by treatment at elevated temperature to give the compounds of formula C.

The ring closure to give the corresponding phenyl-1-indanones of the formula D is carried out by reaction with chlorinating reagents, such as, for example, $SOCl_2$, to give the corresponding acid chlorides and subsequent cyclization by means of a Friedel-Crafts catalyst in an inert solvent, such as, for example, $AlCl_3$ or polyphosphoric acid in methylene chloride or $CS_2$.

The conversion to the 7-phenylindene derivatives of the formula E is carried out by reduction using a hydride-transferring reagent, such as, for example, sodium borohydride or lithium aluminum hydride or hydrogen and an appropriate catalyst in an inert solvent, such as, for example, diethyl ether or tetrahydrofuran, to give the corresponding alcohols and dehydration of the alcohols under acidic conditions, such as, for example, p-toluene-sulfonic acid or an aqueous mineral acid, or by reaction with dehydrating substances, such as magnesium sulfate, anhydrous copper sulfate or molecular sieve.

The preparation of the ligand systems of the formula G and the conversion to the bridged, chiral metallocenes of the formula H and the isolation of the desired racemic form are known in principle. To this end, the phenylindene derivative of the formula E is deprotonated using a strong base, such as, for example, butyllithium or potassium hydride in an inert solvent, and is reacted with a reagent of the formula F to give the ligand system of the formula G. This is subsequently deproteinated by means of two equivalents of a strong base, such as, for example butyllithium or potassium hydride in an inert solvent, and is reacted with the appropriate metal tetrahalide, such as, for example, zirconium tetrachloride, in a suitable solvent. Suitable solvents are aliphatic or aromatic solvents, such as, for example, hexane or toluene, ethereal solvents, such as, for example, tetrahydrofuran or diethyl ether, or halogenated hydrocarbons, such as, for example, methylene chloride or halogenated aromatic hydrocarbons, such as, for example, o-dichlorobenzene. Separation of the racemic and meso forms is effected by extraction or recrystallization using suitable solvents.

The derivatization to give the metallocenes of the formula I can be carried out, for example, by reaction with alkylating agents, such as methyllithium.

Metallocenes I according to the invention are highly active catalyst components for the polymerization of olefins. The chiral metallocenes are preferably employed as racemates. However, it is also possible to use the pure enantiomers in the (+) or (−) form. The pure enantiomers allow an optically active polymer to be prepared. However, the meso form of the metallocenes should be removed, since the polymerization-active center (the metal atom) in these compounds is no longer chiral due to the mirror symmetry at the central metal atom and it is therefore not possible to produce a highly isotactic polymer. If the meso form is not removed, atactic polymer is formed in addition to isotactic polymer. For certain applications, for example soft moldings, this may be entirely desirable.

According to the invention, the cocatalyst used is preferably an aluminoxane of the formula IIa for the linear type and/or of the formula IIb for the cyclic type

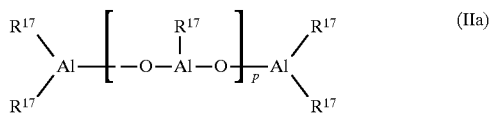

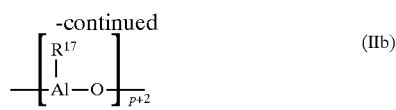

where, in the formulae IIa and IIb, the radicals $R^{17}$ may be identical or different and are a $C_1$–$C_6$-alkyl group, a $C_6$–$C_{18}$-aryl group, benzyl or hydrogen, and p is an integer from 2 to 50, preferably 10 to 35.

Radicals $R^{17}$ are preferably identical and are preferably methyl, isobutyl, phenyl or benzyl, particularly preferably methyl.

If the radicals $R^{17}$ are different, they are preferably methyl and hydrogen or alternatively methyl and isobutyl, where hydrogen or isobutyl is preferably present to the extent of 0.01–40% (number of radicals $R^{17}$).

The aluminoxane can be prepared in various ways by known processes. One of the methods is, for example, to react an aluminum hydrocarbon compound and/or a hydridoaluminum hydrocarbon compound with water (in gas, solid, liquid or bound form—for example as water of crystallization) in an inert solvent (such as, for example toluene). In order to prepare an aluminoxane containing different radicals $R^{17}$, two different trialkylaluminum compounds, for example, according to the desired composition are reacted with water.

The precise structure of the aluminoxanes IIa and IIb is unknown.

Irrespective of the preparation method, all aluminoxane solutions have in common a varying content of unreacted aluminum starting compound, which is in free form or as an adduct.

It is possible to preactivate metallocene by means of aluminoxane of the formula IIa and/or IIb before use in the polymerization reaction. This significantly increases the polymerization activity and improves the grain morphology. Preactivation of the transition-metal compound is carried out in solution. The metallocene is preferably dissolved in a solution of the aluminoxane in an inert hydrocarbon. Suitable inert hydrocarbons are aliphatic or aromatic hydrocarbons. Toluene is preferred.

The concentration of the aluminoxane in the solution is in the range from about 1% by weight to the saturation limit, preferably from 5 to 30% by weight, in each case based on the total amount of solution. The metallocene can be employed in the same concentration, but is preferably employed in an amount of from $10^{-4}$ to 1 mol per mol of aluminoxane. The preactivation is carried out for from 5 minutes to 60 hours, preferably for from 5 to 60 minutes. The temperature is –78° to 100° C., preferably from 0° to 70° C.

The metallocene can be used to carry out a prepolymerization, preferably using the (or one of the) olefin(s) employed in the polymerization.

The metallocene can also be applied to a support. Suitable support materials are, for example, silica gels, aluminum oxides, solid aluminoxane or other inorganic support materials, such as, for example, magnesium chloride. Another suitable support material is a polyolefin powder in finely divided form.

It is preferred to apply the cocatalyst, i.e. the organoaluminum compound, to a support, such as, for example, silica gels, aluminum oxides, solid aluminoxane, other inorganic support materials or alternatively a polyolefin powder in finely divided form, and then to react it with the metallocene.

Inorganic supports which can be employed are oxides produced by flame pyrolysis by combustion of element halides in an oxyhydrogen flame, or can be prepared as silica gels in certain particle size distributions and particle shapes.

The preparation of the supported cocatalyst can be carried out, for example, as described in EP 92 107 331.8 in the following way in an explosion-proofed stainless-steel reactor with a 60 bar pump system, with inert-gas supply, temperature control by jacket cooling and second cooling circuit via a heat exchanger on the forced-circulation system. The pump system aspirates the reactor contents via a connection in the reactor bottom and forces them into a mixer and back into the reactor through a rising line via a heat exchanger. The mixture is designed so that the feed contains a narrowed tube cross section, where an increased flow rate is produced and in whose turbulence zone a narrow feed line is installed axially and against the flow direction and which can be fed—in cycles—in each case with a defined amount of water under 40 bar of argon. The reaction is monitored via a sampler in the pump circuit.

In principle, however, other reactors are also suitable.

In the above-described reactor having a volume of 16 $dm^3$, 5 $dm^3$ of decane are introduced under inert conditions. 0.5 $dm^3$ (=5.2 mol) of trimethylaluminum are added at 25° C. 250 g of silica gel SD 3216-30 (Grace AG) which had previously been dried at 120° C. in an argon fluidised bed are then metered into the reactor through a solids funnel and homogeneously distributed with the aid of the stirrer and the pump system. A total amount of 76.5 g of water is introduced to the reactor in portions of 0.1 $cm^3$ every 15 seconds over the course of 3.25 hours. The pressure, caused by argon and the evolved gases, is kept constant at 10 bar by a pressure-regulation valve. When all the water has been introduced, the pump system is switched off and the stirring is continued for a further 5 hours at 25° C.

The supported cocatalyst prepared in this way is employed as a 10% strength suspension in n-decane. The aluminum content is 1.06 mmol of Al per $cm^3$ of suspension. The isolated solid contains 31% by weight of aluminum, and the suspension medium contains 0.1% by weight of aluminum.

Further ways of preparing a supported cocatalyst are described in EP 92 107331.8.

The metallocene according to the invention is then applied to the supported cocatalyst by stirring the dissolved metallocene with the supported cocatalyst. The solvent is removed and replaced by a hydrocarbon in which both the cocatalyst and the metallocene are insoluble.

The reaction to give the supported catalyst system is carried out at a temperature of from –20° to +120° C., preferably at from 0° to 100° C., particularly preferably at from 15° to 40° C. The metallocene is reacted with the supported cocatalyst by combining the cocatalyst as a from 1 to 40% strength by weight suspension, preferably with a from 5 to 20% strength by weight suspension, in an aliphatic, inert suspension medium, such as n-decane, hexane, heptane or diesel oil, with a solution of the metallocene in an inert solvent, such as toluene, hexane, heptane or dichloromethane, or with the finely ground solid of the metallocene. Conversely, it is also possible to react a solution of the metallocene with the solid of the cocatalyst.

The reaction is carried out by vigorous mixing, for example by stirring at a molar Al/$M^1$ ratio of from 100/1 to 10,000/1, preferably from 100/1 to 3,000/1, and for a reaction time of from 5 to 120 minutes, preferably from 10 to 60 minutes, particularly preferably from 10 to 30 minutes, under inert conditions.

During the reaction time for the preparation of the supported catalyst system, in particular on use of metallocenes according to the invention having absorption maxima in the visible region, changes in the color of the reaction mixture occur which can be used to monitor the progress of the reaction.

When the reaction time is complete, the supernatant solution is separated off, for example by filtration or decanting. The solid which remains is washed from 1 to 5 times with an inert suspension medium, such as toluene, n-decane, hexane, diesel oil or dichloromethane, in order to remove soluble constituents in the catalyst formed, in particular to remove unreacted and thus soluble metallocene.

The supported catalyst system prepared in this way can be dried in vacuo as a powder or resuspended with adhering solvent and metered into the polymerization system as a suspension in one of the abovementioned inert suspension media.

According to the invention, compounds of the formulae $R^{18}_x NH_{4-x} BR^{19}_4, R^{18}_x PH_{4-x} BR^{19}_4, R^{18}_3 CBR^{19}_4$ and $BR^{19}_3$ can be used as suitable cocatalysts in place of or in addition to an aluminoxane. In these formulae, x is a number from 1 to 4, preferably 3, the radicals $R^{18}$ are identical or different, preferably identical, and are $C_1$–$C_{10}$-alkyl, $C_6$–$C_{18}$-aryl or 2 radicals $R^{18}$, together with the atom connecting them, form a ring, the radicals $R^{19}$ are identical or different, preferably identical, and are $C_6$–$C_{18}$-aryl, which may be substituted by alkyl, haloalkyl or fluorine. In particular, $R^{18}$ is ethyl, propyl, butyl or phenyl and $R^{19}$, phenyl, pentafluorophenyl, 3,5-bistrifluoromethylphenyl, mesityl, xylyl or tolyl (cf. EP 277 003, EP 277 004 and EP 426 638).

If the abovementioned cocatalysts are used, the actual (active) polymerization catalyst comprises the product of the reaction of the metallocene and one of said compounds. For this reason, this reaction product is preferably prepared in advance outside the polymerization reactor in a separate step using a suitable solvent.

In principle, the cocatalyst can be, according to the invention, any compound which, due to its Lewis acidity, is able to convert the neutral metallocene into a cation and stabilize the latter ("labile coordination"). In addition, the cocatalyst or the anion formed therefrom should not undergo any further reactions with the metallocene cation formed (cf. EP 427 697).

In order to remove catalyst poisons present in the olefin, purification using an alkylaluminum compound, for example trimethylaluminum or triethylaluminum, is advantageous. This purification can be carried out either in the polymerization system itself, or the olefin is brought into contact with the Al compound before introduction into the polymerization system and is subsequently removed again.

The polymerization or copolymerization is carried out in a known manner in solution, in suspension or in the gas phase, continuously or batchwise, in one or more steps, at a temperature of from –60° to 200° C., preferably from 30° to 80° C., particularly preferably from 50° to 80° C. The polymerization or copolymerization is carried out using olefins of the formula $R^a$—CH=CH—$R^b$. In this formula, $R^a$ and $R^b$ are identical or different and are a hydrogen atom or an alkyl radical having 1 to 14 carbon atoms. However, $R^a$ and $R^b$ may alternatively form a ring together with the carbon atoms connecting them. Examples of such olefins are ethylene, propylene, 1-butene, 1-hexene, 4-methyl-1-pentene, 1-octene, norbornene and norbornadiene. In particular, propylene and ethylene are polymerized.

If necessary, hydrogen is added as a molecular-weight regulator and/or in order to increase the activity. The overall pressure polymerization system is from 0.5 to 100 bar. Polymerization is preferably carried out in the industrially particularly interesting pressure range from 5 to 64 bar.

The metallocene is used in the polymerization in a concentration, based on the transition metal, of from $10^{-3}$ to $10^{-8}$ mol, preferably from $10^{-4}$ to $10^{31\ 7}$ mol, of transition metal per $dm^3$ of solvent or per $dm^3$ of reactor volume. The aluminoxane is used in a concentration of from $10^{-5}$ to $10^{-1}$ mol, preferably from $10^{-4}$ to $10^{-2}$ mol, per $dm^3$ of solvent or per $dm^3$ of reactor volume. The other cocatalysts mentioned are used in an approximately equimolar amount with respect to the metallocene. In principle, however, higher concentrations are also possible.

If the polymerization is carried out as a suspension or solution polymerization, an inert solvent which is customary for the Ziegler low-pressure process is used. For example, the polymerization is carried out in an aliphatic or cycloaliphatic hydrocarbon; examples which may be mentioned are propane, butane, hexane, heptane, isooctane, cyclohexane and methylcyclohexane. It is furthermore possible to use a benzine or hydrogenated diesel oil fraction. Toluene can also be used. The polymerization is preferably carried out in the liquid monomer.

If inert solvents are used, the monomers are metered in in gas or liquid form.

The polymerization can have any desired duration, since the catalyst system to be used according to the invention exhibits only a slight time-dependent drop in polymerization activity.

Before addition of the catalyst, in particular of the supported catalyst system (comprising a metallocene according to the invention and a supported cocatalyst or a metallocene according to the invention and an organo-aluminum compound on a polyolefin powder in finely divided form), another alkylaluminum compound, such as, for example, trimethylaluminum, triethylaluminum, triisobutylaluminum, trioctylaluminum or isoprenylaluminum, may additionally be introduced into the reactor in order to render the polymerization system inert (for example to remove catalyst poisons present in the olefin). This compound is added to the polymerization system in a concentration of from 100 to 0,01 mmol of Al per kg of reactor contents. Preference is given to triisobutylaluminum and triethylaluminum in a concentration of from 10 to 0.1 mmol of Al per kg of reactor contents. This allows the molar Al/$M^1$ ratio to be selected at a low level in the synthesis of a supported catalyst system.

In principle, however, the use of further substances for catalysis of the polymerization reaction is unnecessary, i.e. the systems according to the invention can be used as the only catalysts for the polymerization of olefins.

The process according to the invention is distinguished by the fact that the metallocenes described give polymers of very high molecular weight, in the case of prochiral monomers very high molecular weight and very high stereotacticity, with high catalyst activities in the industrially particularly interesting temperature range from 50° to 80° C.

In particular, the zirconocenes according to the invention are distinguished by the fact that, in the case of stereospecific polymerization of prochiral olefins, for example polypropylene, polymers of high isotacticity are obtained.

In particular in the case of isospecific polymerization of propylene, isotactic polypropylene having long isotactic sequence lengths and high melting point are obtained.

In addition, the catalyst systems supported according to the invention prevent reactor deposits.

The examples below serve to illustrate the invention in greater detail.

All glass equipment was dried by heating in vacuo and was flushed with argon. All operations were carried out in Schlenk vessels with exclusion of moisture and oxygen. The solvents used were in each case freshly distilled over Na/K alloy under argon and stored in Schlenk vessels.

The determination of the Al/CH$_3$ ratio in the aluminoxane was carried out by decomposition of the sample using H$_2$SO$_4$ and determination of the volume of the resultant hydrolysis gases under standard conditions and by complexometric titration of the aluminum in the sample, then dissolved, by the Schwarzenbach method.

For Example Nos. 3 to 5 with the supported aluminum compound (methylaluminoxane on silica gel), referred to below as "MAO on SiO$_2$", an approximately 10% strength by weight suspension in n-decane was prepared, containing, according to aluminum determination, 60 mg of Al/cm$^3$.

For Examples 26 to 30 with the supported aluminum compound (methylaluminoxane on silica gel SD 3216-30/ Grace), referred to below as "FMAO on SiO$_2$", a solvent-free powder was used containing 20% by weight of aluminum in the solid.

Toluene-soluble methylaluminoxane was employed as a 10% strength by weight toluene solution for the examples for suspension polymerization and for bulk polymerization with unsupported metallocene and contained, according to aluminum determination, 36 mg of Al/cm$^3$. The mean degree of oligomerization, according to freezing point depression in benzene, was n=20. For the toluene-soluble methylaluminoxane, an Al:CH$_3$ ratio of 1:1.55 was determined.

The following abbreviations are used

VI=viscosity index in cm$^3$/g

M$_w$=weight average molecular weight in g/mol (determined by gel permeation chromatography)

M$_w$/M$_n$=molecular weight dispersity

M.p.=melting point in °C. (determined by DSC, heating/cooling rate 20° C./min)

II=Isotactic index (II=mm+1.2 mr, determined by $^{13}$C-NMR spectroscopy)

MFI 230/5=meltflow index, measured in accordance with DIN 53735, in dg/min

BD=polymer bulk density in g/dm$^3$.

Synthesis of the metallocenes I used in the polymerization examples (the starting materials employed are commercially available):

A. rac-Dimethylsilylbis(2-methyl-4-phenyl-indenyl) zirconium dichloride (5)

1. (±)-2-(2-phenylbenzyl)propionic acid (1)

48.6 g (0.279 mol) of diethylmethyl malonate were added dropwise at room temperature to 6.5 g (0.285 mol) of sodium in 160 cm$^3$ of H$_2$O-free EtOH. 70.4 g (0.285 mol) of 2-phenylbenzyl bromide in 20 cm$^3$ of H$_2$O-free EtOH were subsequently added dropwise, the batch was refluxed for 3 hours. The solvent was stripped off, and 200 cm$^3$ of H$_2$O were added to the residue. The organic phase was separated off, and the aqueous phase was saturated with NaCl and extracted twice with 200 cm$^3$ of Et$_2$O in each case. The organic phase combined with the extracts was dried (MgSO$_4$).

The residue remaining after the solvent had been stripped off was taken up in 500 cm$^3$ of EtOH and 50 cm$^3$ of H$_2$O, and 56 g (1 mol) of KOH were added. The reaction mixture was refluxed for 4 hours. The solvent was stripped off in vacuo, the residue was taken up in 500 cm$^3$ of H$_2$O and the solution was acidified to pH 1 by means of concentrated aqueous HCl. The precipitate which deposited was filtered off with suction and heated for 30 minutes at 250° C. in a bulb tube with vigorous foaming, giving 58.3 g (85%) of 1 as a viscous oil.

$^1$H-NMR (100 MHz, CDCl$_3$): 11.7 (s, 1H, COOH), 7.1–7.5 (m, 9H, arom. H) 2.3–3.2 (m, 3H, CH and CH$_2$), 0.9 (d, 3H, CH$_3$).

2. (±)-2-Methyl-4-phenylindan-1-one (2)

A solution of 58 g (0.242 mol) of 1 in 60 cm$^3$ (0.83 mol) of thionyl chloride was stirred at room temperature for 18 hours. Excess thionyl chloride was removed at 10 mbar, and the oily residue was freed from adhering residues of thionyl chloride by repeated dissolution in 100 cm$^3$ of toluene in each case and stripping off in vacuo.

The acid chloride was taken up in 150 cm$^3$ of toluene and added dropwise at 10° C. to a suspension of 48 g (0.363 mol) of AlCl$_3$ in 400 cm$^3$ of toluene. When the addition was complete, the mixture was refluxed for a further 3 hours. The reaction mixture was poured into 500 g of ice and acidified to pH 1 by means of concentrated aqueous HCl. The organic phase was separated off, the aqueous phase was then extracted three times with 100 cm$^3$ of Et$_2$O in each case. The combined organic phases were washed with saturated aqueous NaHCO$_3$ solution and saturated aqueous NaCl solution and then dried (MgSO$_4$), giving 50.4 g (93%) of 2, which was reacted further without further purification.

$^1$H-NMR (100 MHz, CDCl$_3$): 7.2–7.8 (m, 8H, arom. H), 3.3 (dd, 1H, β-H), 2.5–2.9 (m, 2H, α- and β-H), 1.3 (d, 3H, CH$_3$).

3. 2-Methyl-7-phenylindene (3)

50 g (0.226 mmol) of 2 were dissolved in 450 cm$^3$ of THF/MeOH (2:1), and 12.8 g (0.34 mol) of sodium borohydride were added in portions at 0° C. with stirring. The reaction mixture was stirred for a further 18 hours and poured into ice, concentrated HCl was added to pH 1 and the mixture was extracted a number of times with Et$_2$O. The combined organic phases were washed with saturated aqueous NaHCO$_3$ solution and NaCl solution and then dried (MgSO$_4$). The solvent was removed in vacuo, and the crude product, without further purification, was taken up in 1 dm$^3$ of toluene, 2 g of p-toluene sulfonic acid were added, and the mixture was refluxed for 2 hours. The reaction mixture was washed with 200 cm$^3$ of saturated aqueous NaHCO$_3$ solution, and the solvent was removed in vacuo. The crude product was purified by filtration through 500 g of silica gel (hexane/CH$_2$Cl$_2$), giving 42 g (90%) of 3 as a colorless oil.

$^1$H-NMR (100 MHz, CDCl$_3$): 7.0–7.6 (m, 8H, arom. H), 6.5 (m, 1H, H—C(3)), 3.4 (s, 2H, CH$_2$), 2.1 (s, 3H, CH$_3$).

4. Dimethylbis(2-methyl-4-phenylindenyl)silane (4)

29 cm$^3$ (73 mmol) of a 2.5M solution of butyllithium in hexane were added at room temperature under argon to a solution of 15 g (72.7 mmol) of 3 in 200 cm$^3$ of H$_2$O- and O$_2$-free toluene and 10 cm$^3$ of H$_2$O- and O$_2$-free THF and heated at 80° C. for 1 hour. The batch was subsequently cooled to 0° C., and 4.7 g (36.4 mmol) of dimethyldichlorosilane were added. The mixture was heated at 80° C. for 1 hour and subsequently poured into 100 cm$^3$ of H$_2$O. The mixture was extracted a number of times with Et$_2$O, and the combined organic phases were dried (MgSO$_4$). The crude product remaining after the solvent had been stripped off was chromatographed on 300 g of silica gel (hexane/CH$_2$Cl$_2$), giving 12.0 g (70%) of 4.

$^1$H-NMR (100 MHz, CDCl$_3$): 7.10–7.70 (m, 16H, arom. H), 6.80 (m, 2H, H—C(3)), 3.80 (s, 2H, H—C(1)), 2.20 (m, 6H, CH$_3$) –0.20 (m, 6H, CH$_3$Si).

5. rac-Dimethylsilylbis(2-methyl-4-phenyl-indenyl) zirconium dichloride (5)

10.6 cm$^3$ (26 mmol) of a 2.5M solution of butyllithium in hexane were added at room temperature under argon to a solution of 6.0 g (12.9 mmol) of 4 in 100 cm$^3$ of H$_2$O- and O$_2$-free toluene, and the mixture was refluxed for 3 hours.

The suspension of the dilithio salt was subsequently cooled to −25° C., and 3.2 g (13.6 mmol) of zirconium tetrachloride were added. The batch was warmed to room temperature over the course of 1 hour, stirred for a further hour and then filtered through a G3 frit. The residue was extracted with 50 cm$^3$ of toluene, and the combined filtrates were freed from solvent under an oil-pump vacuum, giving 9.0 g of the metallocene in the form of a yellow powder as a mixture of the racemic and meso forms in the ratio 1:1. Pure racemate (5) was isolated by stirring the crude mixture a number of times with 20 cm$^3$ of methylene chlorine in each case, the racemate remaining as a yellow crystal powder and the meso form being washed out. 2.74 g (33%) of the pure racemate were obtained.

$^1$H-NMR (300 MHz, CDCl$_3$): 7.0–7.7 (m, 16H, arom. H), 6.9 (s, 2H, H—C(3)), 2.2 (s, 6H, CH$_3$), 1.3 (m, 6H, CH$_3$Si). Molecular weight: 626 M$^+$, correct decomposition pattern.

EXAMPLE B rac-Methylphenylsilanediylbis-(2-methyl-4-phenyl-indenyl)zirconium dichloride (7)

1. Methylphenylbis-(2-methyl-4-phenylindenyl) silane (6)

21 ml (52 mmol) of a 2.5M solution of butyllithium in hexane were added at room temperature under argon to a solution of 10.3 g (50 mmol) of 3 in 90 ml of H$_2$O- and O$_2$-free toluene and 10 ml of H$_2$O- and O$_2$-free THF. The mixture was heated at 80° C. for 1 hour and subsequently cooled to 0° C. 4.8 g (25 mmol) of methylphenyldichlorosilane were added, and stirring was continued overnight at room temperature. The precipitated LiCl was separated off by filtration, and the crude product remaining after the solvent had been stripped off in vacuo was chromatographed on 300 g of silica gel (hexane/CH$_2$Cl$_2$ 9:1), giving 4.6 g (35%) of 6.

$^1$H-NMR (100 MHz, CDCl$_3$): 7.0–7.8 (m, 16H, arom. H), 6.9 (m, 2H, H—C(3)), 3.9 (m, 2H, H—C(1)), 2.3 (m, 6H, CH$_3$), −0.1 (s, 3H, CH$_3$Si).

2. rac-Methylphenylsilanediylbis(2-methyl-4-phenyl-indenyl)zirconium dichloride (7)

3.6 ml (8.9 mmol) of a 2.5M solution of butyllithium in hexane were added at room temperature under argon to 2.3 g (4.4 mmol) of 6 in 25 ml of H$_2$O- and O$_2$-free toluene, and the mixture was heated at 80° C. for 3 hours. The suspension of the dilithio salt was subsequently cooled to −30° C., and 1.1 g (4.5 mmol) of zirconium tetrachloride were added. The mixture was warmed to room temperature over the course of 1 hour and stirred for a further 1 hour. After filtration through a G3 frit, the solvent was removed from the filtrate, and the residue was crystallized from 10 ml of methylene chloride, giving 0.2 g of the racemic form of 7 as orange crystals.

$^1$H-NMR (100 MHz, CDCl$_3$): 7.0–8.2 (m, 21H, arom. H), 6.9 (m, 2H, H—C(3)), 2.4 (s, 3H, CH$_3$), 2.0 (s, 3H, CH$_3$), 1.3 (s, 3H, CH$_3$Si). Mass spectrum: 690 M$^+$, correct decomposition pattern.

EXAMPLE C rac-Dimethylsilandiylbis(4-phenylindenyl)zirconium dichloride (12)

1. 3-(2-phenylphenyl)propionic acid (8)

93 cm$^3$ (0.61 mmol) of diethyl malonate dissolved in 50 cm$^3$ of H$_2$O-free EtOH were added dropwise at room temperature to 14 g (0.61 mmol) of sodium in 400 cm$^3$ of H$_2$O-free EtOH. 150 g (0.61 mmol) of 2-phenylbenzyl bromide in 200 cm$^3$ of H$_2$O-free EtOH were subsequently added dropwise, and the mixture was refluxed for 3 hours. 102 g (1.83 mol) of KOH dissolved in 150 cm$^3$ of H$_2$O were added at room temperature, and the mixture was refluxed for a further 4 hours. The solvent was removed in vacuo, H$_2$O was added to the residue until the latter dissolved completely, and the mixture was acidified to pH 1 by means of concentrated aqueous HCl. The precipitate which formed was filtered off with suction, dried and heated at 130° C. for 1 hour, giving 112 g (81%) of 8 as a viscous oil.

$^1$H-NMR (100 MHz, CDCl$_3$): 9.1 (s, 1H, COOH), 6.9–7.5 (m, 9H, arom. H), 2.3–3.0 (m, 4H, 2CH$_2$).

2. 4-Phenyl-1-indanone (9)

A solution of 102 g (0.45 mol) of 8 in 37 cm$^3$ (0.5 mol) of thionyl chloride was stirred at room temperature for 18 hours. Excess thionyl chloride was removed at 10 mbar, and the oily residue was freed from adhering residues of thionyl chloride by repeated dissolution in 100 cm$^3$ of toluene in each case and stripping off the toluene in vacuo.

The acid chloride was taken up in 200 cm$^3$ of toluene and added dropwise at 10° C. to a suspension of 72 g (0.54 mol) of AlCl$_3$ in 1000 cm$^3$ of toluene. The reaction mixture was heated at 80° C. for 1 hour, poured into 1000 g of ice and acidified to pH 1 by means of concentrated aqueous HCl. The organic phase was separated off, and the aqueous phase was then extracted 3 times with 200 cm$^3$ of Et$_2$O in each case. The combined organic phases were washed with saturated aqueous NaHCO$_3$ solution and saturated aqueous NaCl solution and subsequently dried (MgSO$_4$), giving 96 g (96%) of 9, which was reacted further without further purification.

$^1$H-NMR (100 MHz, CDCl$_3$): 6.9–7.5 (m, 8H, arom. H), 2.5–3.4 (m, 4H, 2CH$_2$).

3. 7-Phenylindene (10)

23 g (0.62 mol) of NaBH$_4$ were added in portions at 0° C. to a solution of 86 g (0.41 mol) of 9 in 300 cm$^3$ of THF/methanol 2:1. The reaction mixture was stirred at room temperature for 18 hours and poured into 300 g of ice, concentrated aqueous HCl was added to pH 1, and the mixture was extracted a number of times with Et$_2$O. The combined organic phases were washed with saturated aqueous NaHCO$_3$ solution and saturated aqueous NaCl solution, dried (MgSO$_4$) and freed from solvent in vacuo.

The crude product was taken up in 1000 cm$^3$ of toluene, 4.5 g of p-toluenesulfonic acid were added, the reaction mixture was refluxed for 2 hours on a water separator and washed three times with 250 cm$^3$ of saturated aqueous NaHCO$_3$ solution, and the solvent was removed in vacuo. Distillation at 0.1 mbar gave, at 96°–108° C., 33 g (41%) of 10 as a colorless oil.

$^1$H-NMR (100 MHz, CDCl$_3$): 7.1–7.7 (m, 8H, arom. H), 6.9 and 6.5 (2m, 2H, CH), 3.5 (m, 2H, CH$_2$).

4. Dimethylbis(4-phenylindenyl)silane (11)

18.7 cm$^3$ (50 mmol) of a 20% strength solution of butyl-lithium in toluene were added at room temperature to a solution of 10 g (50 mmol) of 10 in 100 cm$^3$ of H$_2$O- and O$_2$-free toluene and 5 ml of H$_2$O- and O$_2$-free THF, and the mixture was heated at 80° C. for 2 hours. The yellow suspension was subsequently cooled to 0° C., and 3.2 g (25 mmol) of dimethyldichlorosilane were added. The reaction mixture was heated at 80° C. for a further 1 hour and subsequently washed with 50 cm$^3$ of H$_2$O. The solvent was removed in vacuo, and the residue was recrystallized from heptane at −20° C., giving 6.7 g (62%) of 11 as colorless crystals (m.p. 109°–110° C.).

$^1$H-NMR (100 MHz, CDCl$_3$): 7.0–7.7 (m, 18H, arom. H and H—C(3)), 6.8 (dd, 2H, H—C(2)), 3.8 (m, 2H, H—C(1)), −0.2, (s, 6H, CH$_3$Si).

5. rac-Dimethylsilanediylbis(4-phenylindenyl)zirconium dichloride (12)

12 cm³ (32 mmol) of a 20% strength solution of butyllithium in toluene were added at room temperature under argon to a solution of 6.6 g (16 mmol) of 11 in 70 cm³ of $H_2O$- and $O_2$-free $Et_2O$, and the mixture was subsequently refluxed for 3 hours. The solvent was removed in vacuo, the residue was filtered through a G3 Schlenk frit with 50 ml of $H_2O$- and $O_2$-free hexane, washed with 50 ml of $H_2O$- and $O_2$-free hexane and dried (0.1 mbar, RT).

The dilithio salt was added at −78° C. to a suspension of 3.6 g (16 mmol) of zirconium tetrachloride in 80 cm³ of methylene chloride, and the mixture was warmed to room temperature over the course of 18 hours with magnetic stirring. The batch was filtered through a G3 frit, and the residue was then extracted in portions with a total of 200 cm³ of methylene chloride. The combined filtrates were freed from solvent in vacuo and recrystallized from methylene chloride/hexane (1:1). 5.6 g of the racemic and meso forms in the ratio 1:1 were obtained. Further recrystallization from methylene chloride gave the racemic complex in the form of yellow crystals.

$^1$H-NMR (100 MHz, $CDCl_3$): 7.0–7.8 (m, 22H, arom. H and H—C(3)), 6.1 (d, 2H, H—C(2)), 1.1 (s, 6H, $CH_3Si$). Mass spectrum: 598 M⁺, correct decomposition pattern.

EXAMPLE D rac-Dimethylsilanediylbis(2-ethyl-4-phenyl-indenyl) zirconium dichloride (17)

1. (±)-2-(2-phenylbenzyl)butyric acid (13)

188 g (1 mol) of diethyl ethylmalonate dissolved in 100 cm³ of $H_2O$-free EtOH are added dropwise at room temperature to 23 g (1 mol) of sodium in 400 cm³ of $H_2O$-free EtOH. 247 g (1 mol) of 2-phenylbenzyl bromide in 300 cm³ of $H_2O$-free EtOH were subsequently added dropwise, and the mixture was refluxed for 3 hours. 170 g (3 mol) of KOH dissolved in 300 cm³ of $H_2O$ were added at room temperature, and the mixture was refluxed for a further 4 hours. The solvent was removed in vacuo, $H_2O$ was added to the residue until the latter had dissolved completely, and the mixture was subsequently acidified to pH 1 by means of concentrated aqueous HCl. The precipitate which formed was filtered off with suction, dried and heated at 130° C. for 1 hour, giving 236 g (93%) of 13 as a viscous oil.

$^1$H-NMR (100 MHz, $CDCl_3$): 10.3 (s, 1H, COOH), 7.0–7.3 (m, 9H, arom. H), 2.5–3.0 (m, 3H, CH and $CH_2$), 1.5–1.9 (m, 2H, $CH_2$), 0.9 (t, 3H, $CH_3$).

2. (±)-2-Ethyl-4-phenyl-1-indanone (14)

A solution of 236 g (0.93 mol) of 13 in 81 cm³ (1.2 mol) of thionyl chloride was stirred at room temperature for 18 hours. Excess thionyl chloride was removed at 10 mbar and the oily residue was freed from adhering residues of thionyl chloride by repeated dissolution in 200 cm³ of toluene in each case and stripping off in vacuo. The acid chloride was taken up in 400 cm³ of toluene and added dropwise at 10° C. to a suspension of 133 g (1.0 mol) of $AlCl_3$ in 2000 cm³ of toluene. The reaction mixture was heated at 80° C. for 1 hour, poured into 2000 g of ice and acidified to pH 1 by means of concentrated aqueous HCl. The organic phase was separated off, and the aqueous phase was then extracted three times with 200 cm³ of $Et_2O$ in each case. The combined organic phases were washed with saturated aqueous $NaHCO_3$ solution and saturated aqueous NaCl solution and subsequently dried ($MgSO_4$), giving 187 g (85%) of 14, which was reacted further without further purification.

$^1$H-NMR (100 MHz, $CDCl_3$): 7.0–7.8 (m, 8H, arom. H), 3.1–3.4 (m, 1H, H—C(3)), 2.5–2.9 (m, 2H,H—C(2)) and H—C(3)), 1.3–2.0 (m, 2H, $CH_2$), 0.9 (t, 3H, $CH_3$).

3. 2-Ethyl-7-phenylindene (15)

8 g (0.21 mol) of $NaBH_4$ were added in portions at 0° C. to a solution of 50 g (0.21 mol) of 14 in 600 cm³ of THF/methanol 2:1, the reaction mixture was stirred at room temperature for 18 hours and poured into 600 g of ice, concentrated aqueous HCl was added to pH 1, and the mixture was extracted a number of times with $Et_2O$. The combined organic phases were washed with saturated aqueous $NaHCO_3$ solution and saturated aqueous NaCl solution and subsequently dried ($MgSO_4$).

The crude product was taken up in 1000 cm³ of toluene, 4.5 g of p-toluenesulfonic acid were added, the reaction mixture was refluxed for 2 hours on a water separator and washed 3 times with 250 cm³ of saturated aqueous $NaHCO_3$ solution, and the solvent was removed in vacuo. Distillation at 0.1 mbar gave, at 135° C., 33 g (72%) of 15 as a colorless oil.

$^1$H-NMR (100 MHz, $CDCl_3$): 7.0–7.5 (m, 8H, arom. H) 6.5 (m, 1H, CH), 3.2 (m, 2H, $CH_2$), 2.5 (dq, 2H, $CH_2$), 1.1 (t, 3H, $CH_3$).

3. Dimethylbis(2-ethyl-4-phenylindenyl)silane (16)

29 cm³ (77 mmol) of a 20% strength solution of butyllithium in toluene were added at room temperature to a solution of 17 g (77 mmol) of 15 in 160 cm³ of $H_2O$- and $O_2$-free toluene and 8 ml of $H_2O$- and $O_2$-free THF, and the mixture was heated at 80° C. for 2 hours. The yellow suspension was subsequently cooled to 0° C., and 5 g (38 mmol) of dimethylchlorosilane were added. The reaction mixture was heated at 80° C. for a further 1 hour and subsequently washed with 100 cm³ of $H_2O$. The solvent was removed in vacuo, and the residue was purified by chromatography on 200 g of silica gel (hexane/methylene chloride 9:1), giving 9 g (47%) of 16 as a viscous oil.

$^1$H-NMR (100 MHz, $CDCl_3$): 6.97–7.4 (m, 16H, arom. H), 6.5 (m, 2H, H—C(3)), 3.7 (m, 2H, H—C(1)), 2.4 (m, 4H, $CH_2$), 1.1 (t, 6H, $CH_3$), −0.1, (s, 6H, $CH_3Si$).

5. rac-Dimethylsilanediylbis(2-ethyl-4-phenyl-indenyl) zirconium dichloride (17)

8.4 cm³ of 20% strength solution of butyllithium in toluene were added at room temperature under argon to a solution of 5.6 g (11 mmol) of 16 in 50 cm³ of $H_2O$- and $O_2$-free $Et_2O$, and the mixture was subsequently refluxed for 3 hours. The solvent was removed in vacuo, and the residue was filtered through a G3 Schlenk frit with 50 ml of $H_2O$- and $O_2$-free hexane, then washed with 50 ml of $H_2O$- and $O_2$-free hexane and dried (0.1 mbar, RT).

The dilithio salt was added at −78° C. to a suspension of 2.5 g (11 mmol) of zirconium tetrachloride in 50 cm³ of methylene chloride, and the mixture was warmed to room temperature over the course of 18 hours with magnetic stirring. The batch was filtered through a G3 frit, and the residue was then extracted in portions with a total of 100 cm³ of methylene chloride. The combined filtrates were freed from solvent in vacuo and recrystallized from toluene/hexane (1:1). 2 g (27%) of the racemic and meso forms in the ratio 1:1 were obtained. Further recrystallization from toluene gave the racemic complex 17 in the form of yellow crystals.

$^1$H-NMR (100 MHz, $CDCl_3$): 6.8–7.7 (m, 16H, arom. H), 6.6 (m, 2H, H—C(3)), 2.3–3.9 (m, 4H, $CH_2$) 1.0–1.4 (m, 12H, $CH_3$ and $CH_3Si$). Mass spectrum: 654M⁺, correct decomposition pattern.

EXAMPLE E rac-Dimethylsilanediylbis(2-methyl-4-(1-naphthyl)
indenyl)zirconium dichloride (24)

1. 2-(1-Naphthyl)toluene (18)

13.9 g (0.57 mol) of magnesium turnings were covered by 150 ml of $H_2O$-free $Et_2O$, and the Grignard reaction was initiated by means of 5 g of 2-bromotoluene and a few grains of iodine. 93 g (0.57 mol) of 1-bromotoluene in 450 ml of $H_2O$-free $Et_2O$ were subsequently added dropwise at such a rate that the reaction mixture was kept at the boil. When the addition was complete, boiling was continued until the magnesium had reacted fully.

The Grignard solution was subsequently added dropwise to a solution of 118 g (0.57 mol) of 1-bromonaphthalene and 3.5 g of bis(triphenylphosphine)nickel dichloride in 800 $cm^3$ of toluene at such a rate that the internal temperature did not exceed 50° C. The mixture was subsequently refluxed for a further 3 hours, 500 ml of 10% strength aqueous HCl were added, the phases were separated, and the organic phase was freed from solvent in vacuo. Filtration through silica gel (hexane) gave 115 g (92%) of 18 as a colorless oil.

$^1$H-NMR (100 MHz, $CDCl_3$): 7.2–8.0 (m, 11H, arom. H), 2.0 (s, 3H, $CH_3$).

2. 2-(1-Naphthyl)benzyl bromide (19)

114 g (0.52 mol) of 18 and 103 g (0.58 mol) of N-bromosuccinimide were dissolved in 2000 $cm^3$ of tetrachloromethane at room temperature, 3 g of azobisisobutyronitrile were added, and the mixture was refluxed for 4 hours. The succinimide which precipitated was filtered off, the solvent was removed in vacuo, and the residue was purified by filtration through 1000 g of silica gel (hexane/methylene chloride 9:1), giving 141 g (82%) of 19 as a colorless lachrymatory oil.

$^1$H-NMR (100 MHz, $CDCl_3$): 7.1–8.0 (m, 11H, arom. H), 4.2 (q, 2H, $CH_2Br$).

3. (±)-2-(2-(1-naphthyl)benzyl)propionic acid (20)

75 g (0.43 mmol) of diethyl methylmalonate dissolved in 50 $cm^3$ of $H_2O$-free EtOH were added dropwise at room temperature to 10 g (0.43 mmol) of sodium in 100 $cm^3$ of $H_2O$-free EtOH. 140 g (0.43 mmol) of 2-phenylbenzyl bromide in 200 $cm^3$ of $H_2O$-free EtOH were subsequently added dropwise, and the mixture was refluxed for 3 hours. 85 g (1.3 mol) of KOH dissolved in 100 $cm^3$ of $H_2O$ were added at room temperature, and the mixture was refluxed for a further 4 hours. The solvent was removed in vacuo, $H_2O$ was added to the residue until the latter had dissolved completely, and the mixture was acidified to pH 1 by means of concentrated aqueous HCl. The precipitate which had formed was filtered off with suction, dried and heated at 130° C. for 1 hour, giving 96 g (77%) of 20 as a viscous oil.

$^1$H-NMR (100 MHz, $CDCl_3$): 10.1 (s, 1H, COOH), 6.9–8.0 (m, 11H, arom. H) 2.3–3.0 (m, 3H, $CH_2$ and CH), 0.8 (d, 3H, $CH_3$).

4. (±)-2-Methyl-4-(1-naphthyl)-1-indanone (21)

A solution of 96 g (0.33 mol) of 20 in 37 $cm^3$ (0.5 mol) of thionyl chloride was stirred at room temperature for 18 hours. Excess thionyl chloride was removed at 10 mbar, and the oily residue was freed from adhering residues of thionyl chloride by repeated dissolution in 100 $cm^3$ toluene in each case and stripping off in vacuo.

The acid chloride was taken up in 200 $cm^3$ of toluene and added dropwise at 10° C. to a suspension of 44 g (0.33 mol) of $AlCl_3$ in 1000 $cm^3$ of toluene, and the reaction mixture was heated at 80° C. for 3 hours, poured into 1000 g of ice and acidified to pH 1 by means of concentrated aqueous HCl. The organic phase was separated off, and the aqueous phase was then extracted three times with 200 $cm^3$ of methylene chloride in each case. The combined organic phases were washed with saturated aqueous $NaCl_3$ solution and saturated aqueous NaCl solution and subsequently dried ($MgSO_4$). Chromatography on 1000 g of silica gel (hexane/methylene chloride) gave 12 g (13%) of 21.

$^1$H-NMR (100 MHz, $CDCl_3$); 7.3–8.0 (m, 10H, arom. H), 2.2–3.2 (m, 3H, $CH_2$ and CH), 1.2 (d, 3H, $CH_3$).

5. 2-Methyl-7-(1-naphthyl)indene (22)

1.3 g (33 mmol) of $NaBH_4$ were added at 0° C. to a solution of 12 g (44 mmol) of 21 in 100 $cm^3$ of THF/methanol 2:1, the reaction mixture was stirred at room temperature for 18 hours and poured into 100 g of ice, concentrated aqueous HCl was added to pH 1, and the mixture was extracted a number of times with $Et_2O$. The combined organic phases were washed with saturated aqueous $NaHCO_3$ solution and saturated aqueous NaCl solution and subsequently dried ($MgSO_4$).

The crude product was taken up in 200 $cm^3$ of toluene, 0.5 g of p-toluene sulfonic acid was added, the reaction mixture was refluxed for 2 hours on a water separator and washed 3 times with 50 $cm^3$ of saturated aqueous $NaHCO_3$ solution, and the solvent was removed in vacuo. Filtration through 200 g of silica gel (hexane/methylene chloride) gave 10 g (86%) of 22 as a colorless oil.

$^1$H-NMR (100 MHz, $CDCl_3$): 7.0–8.0 (m, 10H, arom. H), 6.6 (m, 1H, CH), 3.0 (m, 2H, $CH_2$), 2.0 (m, 3H, $CH_3$).

6. Dimethylbis(2-methyl-4-(1-naphthyl)indenyl)silane (23)

14.4 $cm^3$ (50 mmol) of a 20% strength solution of butyllithium in toluene were added at room temperature to a solution of 10 g (38 mmol) of 22 in 100 $cm^3$ of $H_2O$- and $O_2$-free toluene and 5 ml of $H_2O$- and $O_2$-free THF, and the mixture was heated at 80° C. for 2 hours. The yellow suspension was subsequently cooled to 0° C., and 2.5 g (19 mmol) of dimethyldichlorosilane were added. The reaction mixture was heated at 80° C. for a further 1 hour and subsequently washed with 50 $cm^3$ of $H_2O$. The solvent was removed in vacuo, and the residue was recrystallized from heptane at −20° C., giving 8.2 g (75%) of 23 as colorless crystals.

$^1$H-NMR (100 MHz, $CDCl_3$): 7.2–8.1 (m, 20H, arom. H), 6.4 (m, 2H, H—C(3)), 4.0 (m, 2H, H—C (1)), −0.1, (s, 6H, $CH_3Si$).

7. rac-Dimethylsilanediylbis (2-methyl-4-(1-naphthyl) indenyl)zirconium dichloride (24)

10.5 $cm^3$ of a 20% strength solution of butyllithium in toluene were added at room temperature under argon to a solution of 8.0 g (14 mmol) of 23 in 70 $cm^3$ of $H_2O$- and $O_2$-free $Et_2O$, and the mixture was subsequently refluxed for 3 hours. The solvent was removed in vacuo, and the residue was filtered through a G3 Schlenk frit with 50 ml of $H_2O$- and $O_2$-free hexane, then washed with 50 ml of $H_2O$- and $O_2$-free hexane and dried (0.1 mbar, RT).

The dilithio salt was added at −78° C. to a suspension of 3.2 g (14 mmol) of zirconium tetrachloride in 80 $cm^3$ of methylene chloride, and the mixture was warmed to room temperature over the course of 18 hours with magnetic stirring. The batch was filtered through a G3 frit, and the residue was then extracted in portions with a total of 400 $cm^3$ of methylene chloride. The combined filtrates were freed from solvent in vacuo and recrystallized from methylene chloride. 1.5 g (15%) of the racemic and meso forms in the ratio 1:1 were obtained. Further recrystallization from methylene chloride gave the racemic complex in the form of yellow crystals.

$^1$H-NMR (100 MHz, $CDCl_3$): 7.0–8.0 (m, 22H, arom. H), 6.5 (s, 2H, H—C(3)), 2.2 (s, 6H, $CH_3$), 1.3 (s, 6H, $CH_3Si$).

Mass spectrum: 729 $M^+$, correct decomposition pattern.

EXAMPLE F rac-Dimethylsilanediylbis(2-methyl-4-(2-naphthyl)indenyl)zirconium dichloride (31)

1. 2-(2-Naphthyl)toluene (25)

14 g (0.57 mol) of magnesium turnings were covered by 150 ml of $H_2O$-free $Et_2O$, and the Grignard reaction was initiated by means of 5 g of 2-bromotoluene and a few grains of iodine. 95 g (0.58 mol) of 1-bromotoluene in 450 ml of $H_2O$-free $Et_2O$ were subsequently added dropwise at such a rate that the reaction mixture was kept at the boil. When the addition was complete, boiling was continued until the magnesium had reacted fully.

The Grignard solution was subsequently added dropwise to a solution of 120 g (0.57 mol) of 2-bromonaphthalene and 3.5 g of bis(triphenylphosphine)nickel dichloride in 800 cm$^3$ of toluene at such a rate that the internal temperature did not exceed 50° C. The mixture was subsequently refluxed for a further 3 hours, 500 ml of 10% strength aqueous HCl were added, the phases were separated, and the organic phase was freed from solvents in vacuo. Filtration through silica gel (hexane) gave 107 g (87%) of 25 as a colorless oil.

$^1$H-NMR (100 MHz, CDCl$_3$): 7.0–7.9 (m, 1HR, arom. H), 1.9 (s, 3H, CH$_3$).

2. 2-(2-Naphthyl)benzyl bromide (26)

105 g (0.48 mol) of 25 and 90 g (0.5 mol) of N-bromosuccinimide were dissolved in 2000 cm$^3$ of tetrachloromethane at room temperature, 3 g of azobisisobutyronitrile were added, and the mixture was refluxed for 4 hours. The succinimide which precipitated was filtered off, the solvent was removed in vacuo, and the residue was purified by filtration through 1000 g of silica gel (hexane/methylene chloride 9:1), giving 112 g (79%) of 26 as a colorless lachrymatory oil.

$^1$H-NMR (100 MHz, CDCl$_3$): 6.9–8.0 (m, 11H, arom. H), 4.1 (s, 2H, CH$_2$Br).

3. (±)-2-(2-(2-naphthyl)benzyl)propionic acid (27)

70 g (0.37 mmol) of diethyl methylmalonate dissolved in 50 cm$^3$ of $H_2O$-free EtOH were added dropwise at room temperature to 8.5 g (0.37 mmol) of sodium in 100 cm$^3$ of $H_2O$-free EtOH. 110 g (0.37 mmol) of 26 in 200 cm$^3$ of $H_2O$-free EtOH were subsequently added dropwise, and the mixture was refluxed for 3 hours. 62 g (1.1 mol) of KOH dissolved in 100 cm$^3$ of $H_2O$ were added at room temperature, and the mixture was refluxed for a further 4 hours. The solvent was removed in vacuo, $H_2O$ was added to the residue until the latter had dissolved completely, and the mixture was acidified to pH 1 by means of concentrated aqueous HCl. The precipitate which had formed was filtered off with suction, dried and heated at 130° C. for 1 hour, giving 90 g (84%) of 27 as a viscous oil.

$^1$H-NMR (100 MHz, CDCl$_3$): 10.9 (s, 1H, COOH), 7.0–8.1 (m, 11H, arom. H) 2.3–3.0 (m, 3H, CH$_2$ and CH), 1.0 (d, 3H, CH$_3$).

4. (±)-2-Methyl-4-(2-naphthyl)-1-indanone (28)

A solution of 89 g (0.31 mol) of 27 in 37 cm$^3$ (0.5 mol) of thionyl chloride was stirred at room temperature for 18 hours. Excess thionyl chloride was removed at 10 mbar, and the oily residue was freed from adhering residues of thionyl chloride by repeated dissolution in 100 cm$^3$ of toluene in each case and stripping off in vacuo.

The acid chloride was taken up in 200 cm$^3$ of toluene and added dropwise at 10° C. to a suspension of 44 g (0.33 mol) of AlCl$_3$ in 1000 cm$^3$ of toluene, and the reaction mixture was heated at 80° C. for 3 hours, poured into 1000 g of ice and acidified to pH 1 by means of concentrated aqueous HCl. The organic phase was separated off, and the aqueous phase was then extracted three times with 200 cm$^3$ of methylene chloride in each case. The combined organic phases were washed with saturated aqueous NaHCO$_3$ solution and saturated aqueous NaCl solution and subsequently dried (MgSO$_4$). Chromatography on 1000 g of silica gel (hexane/AeOEt) gave 27 g (33%) of 28.

$^1$H-NMR (100 MHz, CDCl$_3$): 7.1–8.0 (m, 10H, arom. H), 2.2–3.3 (m, 3H, CH$_2$ and CH), 1.1 (d, 3H, CH$_3$).

5. 2-Methyl-7-2-naphthyl)indene (29)

3.8 g (100 mmol) of NaBH$_4$ were added at 0° C. to a solution of 27 g (100 mmol) of 28 in 200 cm$^3$ of THF/methanol 2:1, the reaction mixture was stirred at room temperature for 18 hours and poured into 100 g of ice, concentrated aqueous HCl was added to pH 1, and the mixture was extracted a number of times with Et$_2$O. The combined organic phases were washed with saturated aqueous NaHCO$_3$ solution and saturated aqueous NaCl solution and subsequently dried (MgSO$_4$).

The crude product was taken up in 500 cm$^3$ of toluene, 1.5 g of p-toluene sulfonic acid was added, the reaction mixture was refluxed for 2 hours on a water separator and washed 3 times with 50 cm$^3$ of saturated aqueous NaHCO$_3$ solution, and the solvent was removed in vacuo. Filtration through 200 g of silica gel (hexane/methylene chloride) gave 18.4 g (72%) of 29 as a colorless oil.

$^1$H-NMR (100 MHz, CDCl$_3$): 7.0–8.0 (m, 10H, arom. H), 6.6 (m, 1H, CH), 3.0 (m, 2H, CH$_2$), 2.0 (m, 3H, CH$_3$).

6. Dimethylbis(2-methyl-4-(2-naphthyl)indenyl)silane (30)

26 cm$^3$ (70 mmol) of a 20% strength solution of butyllithium in toluene were added at room temperature to a solution of 18 g (70 mmol) of 29 in 70 cm$^3$ of $H_2O$- and $O_2$-free toluene and 4 ml of $H_2O$- and $O_2$-free THF, and the mixture was heated at 80° C. for 2 hours. The yellow suspension was subsequently cooled to 0° C., and 4.5 g (35 mmol) of dimethyldichlorosilane were added. The reaction mixture was heated at 80° C. for a further 1 hour and subsequently washed with 50 cm$^3$ of $H_2O$. The solvent was removed in vacuo, and the residue was recrystallized from heptane at −20° C., giving 10.8 g (54%) of 30 as colorless crystals.

$^1$H-NMR (100 MHz, CDCl$_3$): 7.0–8.1 (m, 20H, arom. H), 6.4 (m, 2H, H—C(3)), 4.0 (m, 2H, H—C (1)), −0.1, (s, 6H, CH$_3$Si).

7. rac-Dimethylsilanediylbis (2-methyl-4-(2-naphthyl)indenyl)zirconium dichloride (31)

13.6 cm$^3$ of a 20% strength solution of butyllithium in toluene were added at room temperature under argon to a solution of 10.5 g (18 mmol) of 30 in 70 cm$^3$ of $H_2O$- and $O_2$-free $Et_2O$, and the mixture was subsequently refluxed for 3 hours. The solvent was removed in vacuo, and the residue was filtered through a G3 Schlenk frit with 50 ml of $H_2O$- and $O_2$-free hexane, then washed with 50 ml of $H_2O$- and $O_2$-free hexane and dried (0.1 mbar, RT).

The dilithio salt was added at −78° C. to a suspension of 4.2 g (18 mmol) of zirconium tetrachloride in 80 cm$^3$ of methylene chloride, and the mixture was warmed to room temperature over the course of 18 hours with magnetic stirring. The batch was filtered through a G3 frit, and the residue was then extracted in portions with a total of 400 cm$^3$ of methylene chloride. The combined filtrates were freed from solvent in vacuo and recrystallized from methylene chloride. 3.1 g (23%) of the racemic and meso forms in the ratio 1:1 were obtained. Further recrystallization from methylene chloride gave the racemic complex in the form of yellow crystals.

$^1$H-NMR (100 MHz, CDCl$_3$): 7.0–8.0 (m, 22H, arom. H), 6.9 (s, 2H, H—C(3)), 2.2 (s, 6H, CH$_3$), 1.3 (s, 6H, CH$_3$Si).

Mass spectrum: 729M$^+$, correct decomposition pattern.

EXAMPLE G rac-Ethanediylbis(2-methyl-4-phenylindenyl) zirconium dichloride (33)

1. 1,2-Bis(2-methyl-4-phenylindenyl)ethane (32)

90 cm$^3$ (0.24 mol) of a 20% strength solution of butyllithium in toluene were added at room temperature under argon to a solution of 50 g (0.24 mol) of 3 in 500 ml of THF. The mixture was stirred at 60° C. for 2 hours, and cooled to −78° C., 22.5 g (0.12 mol) of dibromoethane were added, and the mixture was warmed to room temperature over the course of 18 hours. The reaction mixture was washed with 50 cm$^3$ of H$_2$O, the solvent was removed in vacuo, and the residue was chromatographed on 500 g of silica gel (hexane/methylene chloride 9:1), giving 2.5 g (5%) of 32 as a yellow oil which solidified slowly at −20° C.

$^1$H-NMR (100 MHz, CDCl$_3$): 7.0–8.1 (m, 20H, arom. H), 6.4 (m, 2H, H—C(3)), 4.0 (m, 2H, H—C (1)), −0.1, (s, 6H, CH$_3$Si).

2. rac-Ethanediylbis(2-methyl-4-phenylindenyl)zirconium dichloride (33)

4 cm$^3$ (10 mmol) of a 20% strength solution of butyllithium in toluene were added at room temperature under argon to a solution of 2.3 g (5 mmol) of 32 in 20 ml of H$_2$O- and O$_2$-free Et$_2$O, and the mixture was refluxed for 3 hours. The solvent was removed in vacuo, the residue was filtered through a G3 Schlenk frit with 30 ml of H$_2$O- and O$_2$-free hexane, then washed with 30 ml of H$_2$O- and O$_2$-free hexane and dried (0.1 mbar, RT).

The dilithio salt was added at −78° C. to a suspension of 1.2 g (5 mmol) of zirconium tetrachloride in 30 cm$^3$ of methylene chloride, and the mixture was warmed to a temperature over the course of 18 hours with magnetic stirring. The batch was filtered through a G3 frit, and the residue was then extracted in portions with a total of 100 cm$^3$ of methylene chloride. The combined filtrates were freed from solvent in vacuo and recrystallized from methylene chloride/hexane. 0.5 g (18%) of the racemic and meso forms in the ratio 1:1 was obtained. Further recrystallization from toluene gave the racemic complex in the form of yellow crystals.

$^1$H-NMR (100 MHz, CDCl$_3$): 7.0–7.7 (m, 16H, arom. H), 6.6 (m, 2H, H—C(3)), 3.4–4.1 (m, 4H, H$_2$C—CH$_2$), 2.1 (s, 6H, CH$_3$). Mass spectrum: 598 M$^+$, correct decomposition pattern.

EXAMPLE H

Me$_2$Si(2-Me-4-Ph-indenyl)$_2$ZrMe[BPh$_4$] (35)

1. rac-Dimethylsilanediylbis(2-Methyl-4-phenyl-indenyl)dimethylzirconium (34)

1 cm$^3$ of a 1.6M (1.6 mmol) solution of methyllithium in Et$_2$O were added at −30° C. to 0.5 g (0.8 mmol) of rac-5 in 10 cm$^3$ of H$_2$O- and O$_2$-free Et$_2$O, and the mixture was stirred at 0° C. for 1 hour. The solvent was subsequently removed in vacuo, and the residue was taken up in 20 cm$^3$ of H$_2$O- and O$_2$-free hexane and filtered off through a G3 frit, giving 0.34 g (72%) of 34. Mass spectrum: 588 M$^+$, correct decomposition pattern.

2. Me$_2$Si(2-Me-4-Ph-Indenyl)$_2$ZrMe[BPh$_4$] (35)

0.2 g (0.3 mmol) of 34 were added at 0° C. to 0.25 g (mmol) of tributylammonium tetraphenylborate in 30 cm$^3$ of toluene. The mixture was warmed to 50° C. with stirring and stirred at this temperature for 15 minutes. An aliquot portion of the solution was used for the polymerization.

EXAMPLE 1

A dry 16 dm$^3$ reactor was first flushed with nitrogen and subsequently with propylene and filled with 10 dm$^3$ of liquid propylene. 30 cm$^3$ of a toluene solution of methylaluminoxane were then added, and the batch was stirred at 30° C. for 15 minutes.

In parallel, 1.1 mg of rac-5 were dissolved in 20 cm$^3$ of a toluene solution of methylaluminoxane (27 mmol of Al) and reacted by standing for 15 minutes. The solution was then introduced into the reactor and heated to the polymerization temperature of 50° C. (4° C./min) by supply of heat, and the polymerization system was kept at 50° C. for 1 hour by cooling. The polymerization was terminated by addition of 20 cm$^3$ of isopropanol. The excess monomer was removed in gas form, and the polymer was dried in vacuo, giving 0.9 kg of polypropylene. The reactor exhibited thin deposits on the internal wall and stirrer. The catalyst activity was 818 kg of PP/g of metallocene×h. VI=905 cm$^3$/g; m.p.=159.4° C.; II=98.8%; mmmm=95.4%; M$_w$=1,100,000 g/mol; M$_w$/M$_n$=2.5.

EXAMPLE 2

The polymerization of Example 1 was repeated with the difference that the catalyst used was 0.9 mg of rac-5 and the polymerization temperature was 70° C. 1.4 kg of polypropylene were obtained. The reactor exhibited thick deposits on the internal wall and stirrer. Catalyst activity was 1,555 kg of PP/g of metallocene×h. VI=719 cm$^3$/g; m.p.=157.7° C.

EXAMPLE 3

22 cm$^3$ of the suspension of "MAO on SiO$_2$" (49 mmol of Al) was introduced under argon into a G3 Schlenk frit, and a solution of 4.5 mg of rac-5 in 10 cm$^3$ of toluene (7.2 µmol of Zr) was added. The reaction mixture was stirred at room temperature for 30 minutes, with a spontaneous color change to red gradually fading. The mixture was subsequently filtered, and the solid was washed 3 times with 10 cm$^3$ of hexane. The hexane-moist filter residue which remained was resuspended in 20 cm$^3$ of hexane for the polymerization.

In parallel, a dry 16 dm$^3$ reactor was flushed first with nitrogen and subsequently with propylene and filled with 10 dm$^3$ of liquid propylene. 3 cm$^3$ of triisobutylaluminum (pure, 12 mmol) were then diluted with 30 cm$^3$ of hexane and introduced into the reactor and the batch was stirred at 30° C. for 15 minutes. A catalyst suspension was subsequently introduced into the reactor and heated to the polymerization temperature of 50° C. (4° C./min), and the polymerization system was kept at 50° C. for 1 hour by cooling. Polymerization was terminated by addition of 20 cm$^3$ of isopropanol. The excess monomer was removed in gas form, and the polymer was dried in vacuo. 300 g of polypropylene powder were obtained. The reactor exhibited no deposits on the internal wall or stirrer. The catalyst activity was 67 kg of PP/g of metallocene×h. VI=1380 cm$^3$/g; m.p.=156° C.

EXAMPLE 4

The synthesis of the supported catalyst system from Example 3 was repeated with the difference that 13 cm$^3$ (29 mmol of Al) of the suspension "MAO on SiO$_2$" and 1.8 mg of rac-5 (2.9 µmol of Zr) were used.

The polymerization was carried out analogously to Example 3 at 70° C. 420 g of polypropylene powder were obtained. The reactor exhibited no deposits on the internal wall or stirrer. The catalyst activity was 233 kg of PP/g of metallocene×h. VI=787 cm$^3$/g; m.p.=149.5° C.

EXAMPLE 5

The synthesis of the supported catalyst system from Example 3 was repeated with the difference that 150 cm$^3$ (335 mmol of Al) of the suspension "MAO on SiO$_2$" and 44.2 mg of rac-5 (70.3 μmol of Zr) were used and the reaction mixture was stirred at room temperature for 60 minutes. The solid was subsequently filtered off and washed 3 times with 50 cm$^3$ of hexane. The hexane-moist filter residue which remained was dried in vacuo to give a free-flowing, pale pink powder. 33.3 g of supported, dry catalyst were obtained.

For the polymerization, 2.98 g of this dry catalyst (4 mg=6.3 μmol of Zr) were resuspended in 20 cm$^3$ of hexane.

The polymerization was carried out analogously to Example 3 at 70° C. 1.05 kg of polypropylene powder were obtained. The reactor exhibited no deposits on the internal wall or stirrer. The catalyst activity was 263 kg of PP/g of metallocene×h. VI=944 cm$^3$/g; m.p.=156° C.

EXAMPLE 6

A dry 1.5 dm$^3$ reactor was flushed with N$_2$ and filled at 20° C. with 750 cm$^3$ of a benzine cut with the boiling range 100°–120° C. from which the aromatic compounds had been removed ("®Exxsol 100/120"). The gas space of the reactor was then flushed free of nitrogen by injecting 8 bar of propylene and releasing the pressure, and repeating this procedure four times. 3.75 cm$^3$ of a toluene solution of methylaluminoxane (10% by weight of MAO) were then added. The reactor contents were then heated to 30° C. over the course of 15 minutes with stirring, and the overall pressure was set at 8 bar by addition of propylene at a stirring rate of 500 rpm.

In parallel, 0.1 mg of rac-5 were dissolved in 1.25 cm$^3$ of a toluene solution of methylaluminoxane and reacted fully by standing for 15 minutes. The solution was then introduced into the reactor, and the polymerization system was heated to a temperature of 50° C. and kept at this temperature for 1 hour by appropriate cooling. The pressure was kept at 8 bar during this time by appropriate supply of propylene, the reaction was then terminated by addition of 2 cm$^3$ of isopropanol, and the polymer was filtered off and dried in vacuo.

16 g of polypropylene were obtained. The reactor exhibited deposits on the internal wall and stirrer. The catalyst activity (CTY$_{red}$) was 20 kg of PP/g of metallocene×h×bar. VI=833 cm$^3$/g; m.p.=159° C.

EXAMPLE 7

The polymerization of Example 6 was repeated with the difference that the polymerization temperature was 60° C.

35 g of polypropylene were obtained. The reactor exhibited deposits on the internal wall and stirrer. The catalyst activity (CTY$_{red}$) was 44 kg of PP/g of metallocene×h×bar. VI=484 cm$^3$/g; m.p.=159° C.

EXAMPLE 8

The polymerization from Example 6 was repeated with the difference that the polymerization temperature was 70° C.

88 g of polypropylene were obtained. The reactor exhibited deposits on the internal wall and stirrer. The catalyst activity (CTY$_{red}$) was 110 kg of PP/g of metallocene×h×bar. VI=414 cm$^3$/g; m.p.=159° C.

EXAMPLES 9–12

The procedure was as in Example 2. However, hydrogen was metered in before the filling with liquid propylene:

| Example | Dm$^2$ (s.t.) of H$_2$ | Metallocene activity [kg of PP/g of Met × h] | VI [cm$^3$/g] |
|---|---|---|---|
| 9 | 1.5 | 1640 | 495 |
| 10 | 3 | 1590 | 212 |
| 11 | 4.5 | 1720 | 142 |
| 12 | 200 | 1580 | 17 |

Examples 9–12 demonstrate the good hydrogen utilization of the metallocene according to the invention. Molecular weight regulation into the wax region (see Example 12) is possible.

EXAMPLE 13

The procedure was as in Example 3. However, 0.2 bar of hydrogen was injected into the reactor before addition of the catalyst, and the polymerization temperature was 60° C. However, ethylene was metered in at a uniform rate during the polymerization. In total, 12 g of ethylene were introduced into the reactor. 0.4 kg of ethylene-copolymer were obtained. The metallocene activity was 88 kg of copolymer/g of metallocene×h. The ethylene content of the polymer was 2.4% by weight, and the ethylene was predominantly incorporated as isolated units. VI=200 cm$^3$/g; melting point 143° C.

EXAMPLE 14

The procedure was as in Example 13. However, a total of 34 g of ethylene were metered in during polymerization. 0.38 kg of ethylene-propylene copolymer containing 7% by weight of ethylene was obtained. VI=120 cm$^3$; melting point 121° C.

EXAMPLE 15

The procedure was as in Example 4. However, 4 g of ethylene were metered in during the polymerization and 0.1 bar of hydrogen was injected before the polymerization. 0.52 kg of ethylene-propylene copolymer were obtained. The metallocene activity was 286 kg of copolymer/g of metallocene×h. The ethylene content of the polymer was 6.1% by weight, and the majority of the ethylene was incorporated as isolated units. VI=150 cm$^3$/g; melting point 116° C.

EXAMPLE 16

A dry 150 dm$^3$ reactor was flushed with nitrogen and filled at 20° C. with 80 dm$^3$ of a benzine cut having the boiling range of 100°–120° C. from which the aromatic compounds had been removed. The gas space was then flushed free of nitrogen by injecting 2 bar of propylene and releasing the pressure, and repeating this procedure four times. After 50 l of liquid propylene had been added, 64 cm$^3$ of a toluene solution of methylaluminoxane (corresponding to 100 mmol of Al, molecular weight 1080 g/mol according to cryoscopic determination) were added, and the reactor contents were heated to 50° C. A hydrogen content of 2.0% was established in the gas space of the reactor by metering in hydrogen and was later kept constant during the 1st polymerization step by subsequent metering in.

9.8 mg of rac-7 were dissolved in 32 ml of the toluene solution of methylaluminoxane (corresponding to 50 mmol of Al) and were introduced into the reactor after 15 minutes. The polymerization was then carried out in a 1st polymerization step for 5 hours at 50° C. The gaseous components were then removed at a reactor pressure of 3 bar, and 2000 g of ethylene gas were fed in. The reactor pressure increased to 8 bar during this operation, and the polymerization was continued for a further 14 hours at 40° C. before the reaction was terminated by means of $CO_2$ gas.

18.6 kg of block copolymer were obtained, corresponding to a metallocene activity of 99.9 kg of copolymer/g of metallocene×h. VI=230 cm$^3$/g; MFI (230/5)=11 dg/min, MFI (230/2.16)=3.7 dg/min; melting point of the polymer in the 1st polymerization step: 159° C., glass transition temperature of the polymer in the 2nd polymerization step: −38° C. The block copolymer contained 5% of ethylene. Fractionation of the product gave the following composition: 69% by weight of homopolymer, 31% by weight of copolymer, the copolymer having an ethylene content of 15% by weight, and the mean $C_2$ block length was 2.2.

EXAMPLE 16a

The procedure was as in Example 16. 3 mg of rac-24 were dissolved in 32 ml of the toluene solution of methylaluminoxane (corresponding to 50 mmol of Al) and were introduced into the reactor after 15 minutes. The polymerization was then carried out in a 1st polymerization step for 2.5 hours at 50° C. The gaseous components were then removed at a reactor pressure of 3 bar, and 3000 g of ethylene gas were fed in. The reactor pressure increased to 8 bar during this operation, and the polymerization was continued for a further 8 hours at 40° C. before the reaction was terminated by means of $CO_2$ gas.

16.5 kg of block copolymer were obtained, corresponding to a metallocene activity of 524 kg of copolymer/g of metallocene×h. VI=480 cm$^3$/g; MFI (230/5)=2 dg/min, melting point of the polymer in the 1st polymerization step: 162° C., glass transition temperature of the polymer in the 2nd polymerization step: −54° C. The block copolymer contained 15% of ethylene.

EXAMPLE 17

The procedure was as in Example 1, but 12.5 mg of metallocene rac-7 were used. 1.5 kg of polypropylene were obtained; the metallocene activity was 120 kg of PP/g of metallocene×h. VI=1050 cm$^3$/g; melting point 159° C.

EXAMPLE 18

The procedure was as in Example 2, but 4.1 mg of metallocene rac-7 were used. 1.3 kg of polypropylene were obtained; the metallocene activity was 317 kg of PP/g of metallocene×h. VI=555 cm$^3$/g; melting point 157° C.

Comparative Example A

The procedure was as in Example 1, but 12.5 mg of rac-phenyl(methyl)silanediylbis(2-methyl-1-indenyl) zirconium dichloride were used. 1.35 kg of polypropylene were obtained; the metallocene activity was 108 kg of PP/g of metallocene×h. VI=1050 cm$^3$/gl; melting point 149° C.

Comparative Example B

The procedure was as in Example 1, but 12.5 mg of rac-phenyl(methyl) silanediylbis(1-indenyl)zirconium dichloride were used. 0.28 kg of polypropylene were obtained; the metallocene activity was 22.4 kg of PP/g of metallocene×h. VI=74 cm$^3$/gl; melting point 141° C.

EXAMPLE 19

The procedure was as in Example 1, but 3.3 mg of 24 were used. 0.78 kg of polypropylene were obtained; metallocene activity was 237 kg of PP/g of metallocene×h. VI=1700 cm$^3$/g; melting point 163° C., $M_w$=2.1×10$^6$ g/mol, MFI230/21.6=1 dg/min; $M_w/M_n$=2.1.

EXAMPLE 19a

The procedure was as in Example 2, but 1.0 mg of rac-24 were used. 1.2 kg of polypropylene were obtained. The metallocene activity was 1200 kg of PP/g of metallocene×h. VI=1100 cm$^3$/g. Melting point=161° C.

EXAMPLE 20

The procedure was as in Example 1; however the polymerization temperature was 40° C. 6.0 mg of 17 were used. 1.95 kg of polypropylene were obtained; the metallocene activity was 325 kg of PP/g of metallocene×h. VI=1320 cm$^3$/g; melting point 162° C., $M_w$=1.79×10$^6$ g/mol, $M_w/M_n$=2.3.

Comparative Example C

The procedure was as in Example 20, but the conventional metallocene rac-dimethylsilanediylbis(2-ethyl-1-indenyl) zirconium dichloride was used. 0.374 kg of polypropylene were obtained; the metallocene activity was 62.3 kg of PP/g of metallocene×h. VI=398 cm$^3$/g; melting point 147° C., $M_w$=450,000 g/mol, $M_w/M_n$=2.5.

EXAMPLE 21

The procedure was as in Example 1, but 5.2 mg of 31 were used. 1.67 kg of polypropylene were obtained; the metallocene activity was 321 kg of PP/g of metallocene×h. VI=980 cm$^3$/g; melting point 158° C.

EXAMPLE 22

The procedure was as in Example 1, but the polymerization was carried out at 30° C. and 3.7 mg of 33 were used. 0.35 kg of polypropylene were obtained; the metallocene activity was 94 kg of PP/g of metallocene×h. VI=440 cm$^3$/g; melting point 153° C.

EXAMPLE 23

A dry 16 dm$^3$ reactor was flushed with propylene and filled with 10 dm$^3$ of liquid propylene. 1.1 cm$^3$ of the reaction product from H.2 (corresponding to 7.5 mg of 34) were then dissolved in 20 cm$^3$ of toluene and introduced into the reactor at 30° C. The reactor was heated to 50° C. (10° C./min) and the polymerization system was kept at this temperature for 1 hour by cooling. The polymerization was terminated by addition of $CO_2$ gas. The excess monomer was removed in gas form, and the polymer was dried in vacuo at 80° C. 2.45 kg of polypropylene were obtained. VI=875 cm$^3$/g; melting point 160° C.

EXAMPLE 24

A dry 16 dm$^3$ reactor was flushed with nitrogen and filled at 20° C. with 10 dm$^3$ of a benzine cut having the boiling range 100°–120° C. from which the aromatic compounds had been removed. The gas space of the reactor was then flushed free of nitrogen by injecting 2 bar of ethylene and releasing the pressure and repeating this operation 4 times. 30 cm$^3$ of a toluene solution of methylaluminoxane (corresponding to 45 mmol of Al, molecular weight 700 g/mol according to cryoscopic determination) were then added. The reactor contents were heated to 30° C. over the course of 15 minutes with stirring, and the overall pressure was set at 5 bar by addition of ethylene at a stirring rate of 250 rpm.

In parallel, 3.2 g of 12 were dissolved in 20 cm³ of a toluene solution of methylaluminoxane and were preactivated by standing for 15 minutes. The solution was then introduced into the reactor, and the polymerization system was heated to a temperature of 50° C. and kept at this temperature for 4 hours by appropriate cooling. The overall pressure was kept at 5 bar during this time by a appropriate supply of ethylene.

The polymerization was terminated by addition of 20 ml of isopropanol, and the polymer was filtered off and dried in vacuo. 0.7 kg of polyethylene were obtained. VI=690 cm³/g.

EXAMPLE 25

The procedure of Example 24 was followed. In contrast to Example 23, 1.8 mg of rac-7 were employed, and the polymerization system was heated to 70° C. and kept at this temperature for 1 hour. 0.9 kg of polyethylene were obtained. VI=730 cm³/g.

EXAMPLE 26

15 g of "F-MAO on $SiO_2$" (111 mmol of Al) were suspended in 100 cm³ of toluene in a stirrable vessel and cooled to −20° C. At the same time, 155 mg (0.246 mmol) of rac-5 were dissolved in 75 cm³ of toluene and added dropwise to this suspension over the course of 30 minutes. The mixture was slowly warmed to room temperature with stirring, the suspension taking on a red color. The mixture was subsequently stirred at 80° C. for 1 hour, cooled to room temperature and filtered, and the solid was washed 3 times with 100 cm³ of toluene in each case and once with 100 cm³ of hexane. The filtrate was red. The hexane-moist filter residue which remained was dried in vacuo, giving 13.2 g of free-flowing, pale red, supported catalyst. Analysis gave a content of 3.2 mg of zirconocene per gram of catalyst.

Polymerization: For the polymerization, 2.08 g of the catalyst were suspended in 50 cm³ of a benzine cut having the boiling range of 100°–120° C. from which the aromatic compounds had been removed. The polymerization was carried out analogously to Example 3 at 60° C. 1100 g of polypropylene powder were obtained. The reactor exhibited no deposits on the internal wall or stirrer. Activity=165 kg of PP/(g of metallocene×h). VI=1100 cm³/g. Melting point=153° C.; $M_w$=1,485,000; $M_w/M_n$=3.2; MFI 230/5=0.1 dg/min; BD=440 g/dm³.

EXAMPLE 27

1.31 g of the catalyst from Example 26 were suspended in 50 cm³ of a benzine cut having the boiling range of 100°–120° C. from which the aromatic compounds had been removed. The polymerization was carried out analogously to Example 3 at 70° C. 1300 g of polypropylene powder were obtained. The reactor exhibited no deposits on the internal wall or stirrer. Activity=310 kg of PP/(g of metallocene×h). VI=892 cm³/g; melting point=150° C., $M_w$=1,290,000; $M_w/M_n$=3.0; BD=410 g/dm³.

EXAMPLE 28

The supporting procedure from Example 26 was repeated with the difference that 0.845 g of rac-5 dissolved in 500 cm³ of toluene were reacted with 90 g of "F-MAO on $SiO_2$" and suspended in 500 cm³ of toluene. 84 g of red, pulverulent catalyst were obtained. Analysis gave a content of 9 mg of metallocene per gram of solid, and the red filtrate contained 13 mg of zirconium.

Polymerization: 1.1 g of the supported catalyst were suspended in 50 ml of a benzine cut having a boiling range of 100°–120° C. from which the aromatic compounds had been removed. The polymerization was carried out analogously to Example 3 at 70° C. 2850 g of polypropylene powder were obtained. The reactor exhibited no deposits on the internal wall or stirrer. Activity=288 kg of PP/(g of metallocene×h); VI=638 cm³/g; melting point=150° C.; MFI 230/5=0.5 dg/min; BD=410 g/dm³.

EXAMPLE 29

A microporous polypropylene powder (AKZO) having a particle size of smaller than 100 μm was freed from impurities by extraction with toluene in a Soxhlet extractor under inert conditions and subsequently washed with 20% strength by weight of trimethylaluminum solution in toluene and dried in vacuo. In parallel, 51.1 mg of rac-5 were dissolved in 40 cm³ of a toluene solution of methylaluminoxane and reacted fully by standing for 15 minutes. 16.5 g of the PP powder were metered in, and the gas in the pores of the support and some of the solvent were removed by briefly applying a vacuum, and the catalyst solution was absorbed fully. Vigorous shaking of the reaction vessel gave 46 g of homogeneous, finely divided and free-flowing red powder. 10 g of the supported catalyst powder were prepolymerized for 30 minutes with ethylene under inert conditions in a rotary evaporator. The ethylene excess pressure was kept constant at 0.1 bar by means of a pressure-regulation valve, and the mixing of the catalyst powder was achieved by continuous rotation of the reaction vessel with cooling at 0° C. 12 g of prepolymerized catalyst were obtained.

Polymerization: 4.6 g of the supported, prepolymerized catalyst were suspended in 50 cm³ of a benzine cut having the boiling range 100°–120° C. from which the aromatic compounds had been removed. Polymerization was carried out analogously to Example 3 at 70° C. 250 g of polypropylene powder were obtained. The reactor exhibited no deposits on the internal wall or stirrer, and the mean particle size was 1,000 μm. Activity=59 kg of PP/(g of metallocene×h); VI=734 cm³/g. Melting point=152° C.; BD=390 g/dm³.

EXAMPLE 30

1 g of the supported, non-prepolymerized catalyst from Example 29 was suspended in 50 cm³ of n-decane for the polymerization. The polymerization was carried out analogously to Example 3 at 70° C. 600 g of polypropylene were obtained. The reactor exhibited thin deposits on the internal wall and stirrer, and the mean particle diameter was >2000 μm. Activity=540 kg of PP/(g of metallocene×h); VI=1400 cm³/g; melting point=157.7° C.; BD=280 g/dm³.

We claim:

1. A compound of formula I

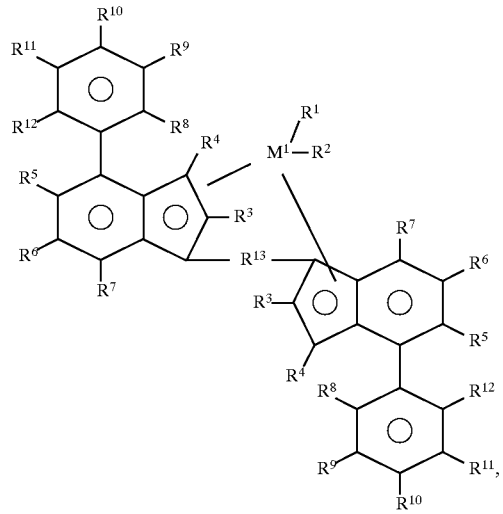

in which

M¹ is a metal from group IVb, Vb or VIb of the Periodic Table, $R^1$ and $R^2$ are identical or different and are a hydrogen atom, a $C_1$–$C_{10}$-alkyl group, a $C_1$–$C_{10}$-alkoxy group a $C_8$–$C_{10}$-aryl group, a $C_6$–$C_{10}$-aryloxy group, a $C_2$–$C_{10}$-alkenyl group, a $C_7$–$C_{40}$-arylalkyl group, a $C_7$–$C_{40}$-alkylaryl group, a $C_8$–$C_{40}$-arylalkenyl group, an OH group or a halogen atom, the radicals $R^3$ are identical or different and are a hydrogen atom, a halogen atom, a $C_1$–$C_{10}$-alkyl group, which may be halogenated, a $C_6$–$C_{10}$-aryl group, an —$NR^{16}_2$, —$SR^{15}$, —$OSiR^{16}_3$, —$SiR^{16}_3$, or —$PR^{16}_2$ radical, in which $R^{16}$ is a halogen atom, a $C_1$–$C_{10}$-alkyl group or a $C_6$–$C_{10}$-aryl group, the radicals $R^8$ are identical or different and are a $C_1$–$C_{10}$-alkyl group, which may be halogenated, a $C_8$–$C_{10}$-aryl group, an —$NR^{16}_2$, —$SR^{16}$, —$OSiR^{16}_3$, —$SiR^{16}_3$ or —$PR^{16}_2$ radical, in which $R^{16}$ is a halogen atom, a $C_1$–$C_{10}$-alkyl group or a $C_8$–$C_{10}$-aryl group, $R^4$ to $R^7$ and $R^9$ to $R^{12}$ are identical or different and are as defined for $R^3$, or adjacent radicals $R^4$ to $R^{12}$, together with the atoms connecting them, form one or more aromatic or aliphatic rings, or the radicals $R^5$ and $R^8$ or $R^{12}$ together with the atoms connecting them, form an aromatic or aliphatic ring, $R^{13}$ is

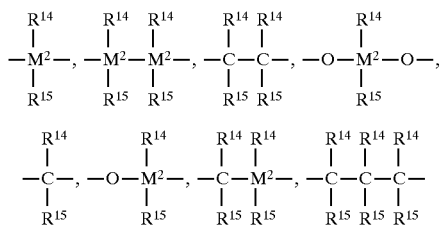

=$BR^{14}$, =$AlR^{14}$, —Ge—, —O—, —S—, =SO, =$SO_2$, =$NR^{14}$, =CO, =$PR^{14}$ or =P(O) $R^{14}$, where $R^{14}$ and $R^{15}$ are identical or different and are a hydrogen atom, a halogen atom, a $C_1$–$C_{10}$-alkyl group, a $C_1$–$C_{10}$-fluoroalkyl group, a $C_1$–$C_{10}$-alkoxy group, a $C_8$–$C_{10}$-aryl group, a $C_8$–$C_{10}$-fluoroaryl group, a $C_8$–$C_{10}$-aryloxy group, a $C_2$–$C_{10}$-alkenyl group, a $C_7$–$C_{40}$-arylalkyl group, a $C_7$–$C_{40}$-alkylaryl group or a $C_8$–$C_{40}$-arylalkenyl group, or $R^{14}$ and $R^{15}$, in each case together with atoms connecting them, form one or more rings; and $M^2$ is silicon, germanium or tin.

2. A compound of formula I

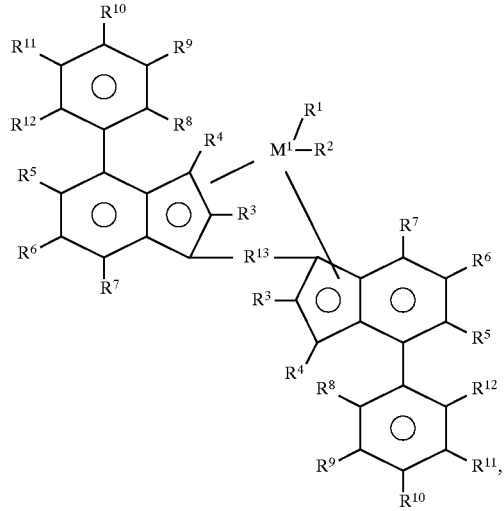

in which $M^1$ is a metal from group IVb, Vb or VIb of the Periodic Table, $R^1$ and $R^2$ are identical or different and are a hydrogen atom, a $C_1$–$C_{10}$-alkyl group, a $C_1$–$C_{10}$-alkoxy group a $C_8$–$C_{10}$-aryl group, a $C_8$–$C_{10}$-aryloxy group, a $C_2$–$C_{10}$-alkenyl group, a $C_7$–$C_{40}$-arylalkyl group, a $C_7$–$C_{40}$-alkylaryl group, a $C_8$–$C_{40}$-arylalkenyl group, an OH group or a halogen atom, the radicals $R^3$ are identical or different and are a hydrogen atom, a halogen atom, a $C_1$–$C_{10}$-alkyl group, which may be halogenated, a $C_8$–$C_{10}$-aryl group, an —$NR^{16}_2$, —$SR^{16}$, —$OSiR^{16}_3$, —$SiR^{16}_3$ or —$PR^{16}_2$ radical, in which $R^{16}$ is a halogen atom, a $C_1$–$C_{10}$-alkyl group or a $C_6$–$C_{10}$-aryl group, the radicals $R^9$ are identical or different and are a $C_1$–$C_{10}$-alkyl group, which may be halogenated, a $C_8$–$C_{10}$-aryl group, an —$NR^{16}_2$, —$SR^{16}$, —$OSiR^{16}_3$, —$SiR^{16}_3$ or —$PR^{16}_2$ radical, in which $R^{16}$ is a halogen atom, a $C_1$–$C_{10}$-alkyl group or a $C_8$–$C_{10}$-aryl group, $R^4$ to $R^8$ and $R_{10}$ to $R^{12}$ are identical or different and are as defined for $R^3$ or adjacent radicals $R^4$ to $R^{12}$, together with the atoms connecting them, form one or more aromatic or aliphatic rings, or the radicals $R^5$ and $R^8$ or $R^{12}$, together with the atoms connecting them, form an aromatic or aliphatic ring, $R^{13}$ is

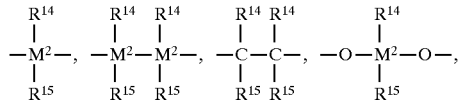

-continued

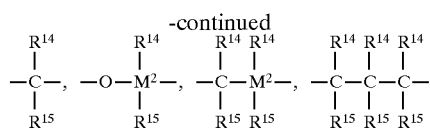

$=BR^{14}$, $=AlR^{14}$, —Ge—, —O—, —S—, $=SO$, $=SO_2$, $=NR^{14}$, $=CO$, $=PR^{14}$ or $=P(O)R^{14}$, where $R^{14}$ and $R^{15}$ are identical or different and are a hydrogen atom, a halogen atom, a $C_1$–$C_{10}$-alkyl group, a $C_1$–$C_{10}$-fluoroalkyl group, a $C_1$–$C_{10}$-alkoxy group, a $C_8$–$C_{10}$-aryl group, a $C_8$–$C_{10}$-fluoroaryl group, a $C_8$–$C_{10}$-aryloxy group, a $C_2$–$C_{10}$-alkenyl group, a $C_7$–$C_{40}$-arylalkyl group, a $C_7$–$C_{40}$-alkylaryl group or a $C_8$–$C_{40}$-arylalkenyl group, or $R^{14}$ and $R^{15}$, in each case together with atoms connecting them, form one or more rings, and $M^2$ is silicon, germanium or tin.

3. A compound of formula I

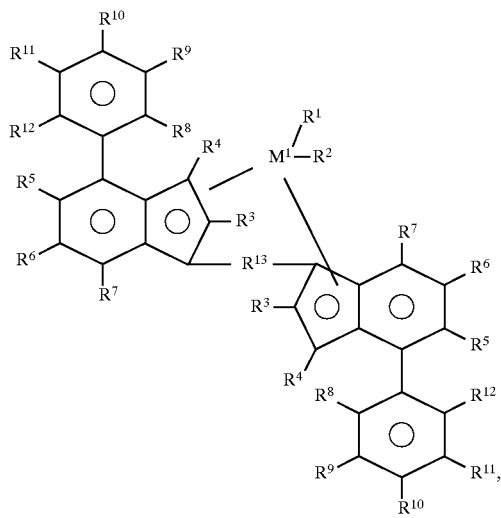

in which $M^1$ is a metal from group IVb, Vb or VIb of the Periodic Table, $R^1$ and $R^2$ are identical or different and are a hydrogen atom, a $C_1$–$C_{10}$-alkyl group, a $C_1$–$C_{10}$-alkoxy group a $C_8$–$C_{10}$-aryl group, a $C_8$–$C_{10}$-aryloxy group, a $C_2$–$C_{10}$-alkenyl group, a $C_7$–$C_{40}$-arylalkyl group, a $C_7$–$C_{40}$-alkylaryl group, a $C_8$–$C_{40}$-arylalkenyl group, an OH group or a halogen atom, the radicals $R^3$ are identical or different and are a hydrogen atom, a halogen atom, a $C_1$–$C_{10}$-alkyl group, which may be halogenated, a $C_8$–$C_{10}$-aryl group, an —$NR^{16}{}_2$, —$SR^{16}$, —$OSiR^{16}{}_3$, —$SiR^{16}{}_3$, or —$PR^{16}{}_2$ radical, in which $R^{16}$ is a halogen atom, a $C_1$–$C_{10}$-alkyl group or a $C_8$–$C_{10}$-aryl group, the radicals $R^{10}$ are identical or different and are a $C_1$–$C_{10}$-alkyl group, which may be halogenated, a $C_6$–$C_{10}$-aryl group, an —$NR^{16}{}_2$, —$SR^{16}$, —$OSiR^{16}{}_3$, —$SiR^{16}{}_3$ or —$PR^{16}{}_2$ radical, in which $R^{16}$ is a halogen atom, a $C_1$–$C_{10}$-alkyl group or a $C_8$–$C_{10}$-aryl group, $R^4$ to $R^9$ and $R^{11}$ to $R^{12}$ are identical or different and are as defined for $R^3$, or adjacent radicals $R^4$ to $R^{12}$, together with the atoms connecting them, form one or more aromatic or aliphatic rings, or the radicals $R^5$ and $R^8$ or $R^{12}$ together with the atoms connecting them, form an aromatic or aliphatic ring, $R^{13}$ is

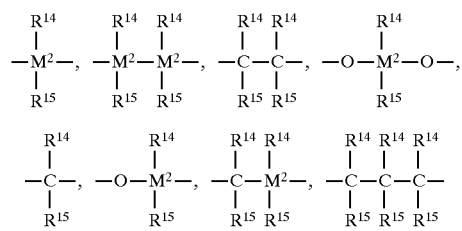

$=BR^{14}$, $=AlR^{14}$, —Ge—, —O—, —S—, $=SO$, $=SO_2$, $=NR^{14}$, $=CO$, $=PR^{14}$ or $=P(O)R^{14}$, where $R^{14}$ and $R^{15}$ are identical or different and are a hydrogen atom, a halogen atom, a $C_1$–$C_{10}$-alkyl group, a $C_1$–$C_{10}$-fluoroalkyl group, a $C_1$–$C_{10}$-alkoxy group, a $C_6$–$C_{10}$-aryl group, a $C_6$–$C_{10}$-fluoroaryl group, a $C_6$–$C_{10}$-aryloxy group, a $C_2$–$C_{10}$-alkenyl group, a $C_7$–$C_{40}$-arylalkyl group, a $C_7$–$C_{40}$-alkylaryl group or a $C_8$–$C_{40}$-arylalkenyl group, or $R^{14}$ and $R^{15}$, in each case together with atoms connecting them, form one or more rings, and $M^2$ is silicon, germanium or tin.

4. A compound of formula I

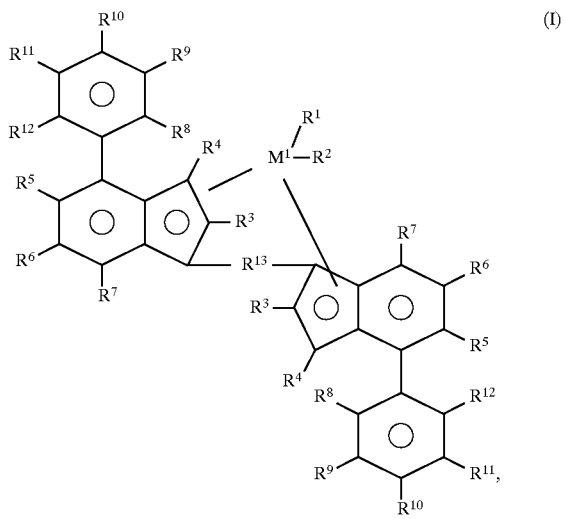

in which $M^1$ is a metal from group IVb, Vb or VIb of the Periodic Table, $R^1$ and $R^2$ are identical or different and are a hydrogen atom, a $C_1$–$C_{10}$-alkyl group, a $C_1$–$C_{10}$-alkoxy group a $C_8$–$C_{10}$-aryl group, a $C_6$–$C_{10}$-aryloxy group, a $C_2$–$C_{10}$-alkenyl group, a $C_7$–$C_{40}$-arylalkyl group, a $C_7$–$C_{40}$-alkylaryl group, a $C_8$–$C_{40}$-arylalkenyl group, an OH group or a halogen atom, the radicals $R^3$ are identical or different and are a hydrogen atom, a halogen atom, a $C_1$–$C_{10}$-alkyl group, which may be halogenated, a $C_6$–$C_{10}$-aryl group, an —$NR^{16}{}_2$, —$SR^{15}$, —$OSiR^{16}{}_3$, —$SiR^{16}{}_3$, or —$PR^{16}{}_2$ radical, in which $R^{16}$ is a halogen atom, a $C_1$–$C_{10}$-alkyl group or a $C_8$–$C_{10}$-aryl group, the radicals $R^{11}$ are identical or different and are a $C_1$–$C_{10}$-alkyl group, which may be halogenated, a $C_6$–$C_{10}$-aryl group, an —$NR^{16}{}_2$, —$SR^{16}$, —$OSiR^{16}{}_3$, —$SiR^{16}{}_3$ or —$PR^{16}{}_2$ radical, in which $R^{16}$ is a halogen atom, a $C_1$–$C_{10}$-alkyl group or a $C_6$–$C_{10}$-aryl group, $R^4$ to $R^{10}$ and $R^{12}$ are identical or different and are as defined for $R^3$, or adjacent radicals $R^4$ to $R^{12}$, together with the atoms connecting them, form one or more aromatic or aliphatic rings, or the radicals $R^5$ and $R^8$ or $R^{12}$ together with the atoms connecting them, form an aromatic or aliphatic ring, $R^{13}$ is

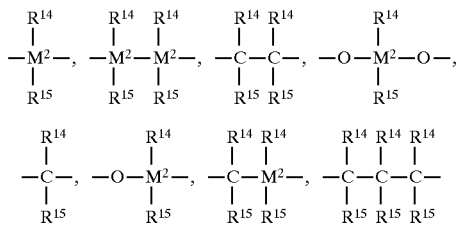

$=BR^{14}$, $=AlR^{14}$, —Ge—, —O—, —S—, $=SO$, $=SO_2$, $=NR^{14}$, $=CO$, $=PR^{14}$ or $=P(O)R^{14}$, where $R^{14}$ and $R^{15}$ are identical or different and are a hydrogen atom, a halogen atom, a $C_1$–$C_{10}$-alkyl group, a $C_1$–$C_{10}$-fluoroalkyl group, a $C_1$–$C_{10}$-alkoxy group, a $C_8$–$C_{10}$-aryl group, a $C_8$–$C_{10}$-fluoroaryl group, a $C_8$–$C_{10}$-aryloxy group, a $C_2$–$C_{10}$-alkenyl group, a $C_7$–$C_{40}$-arylalkyl group, a $C_7$–$C_{40}$-alkylaryl group or a $C_8$–$C_{40}$-arylalkenyl group, or $R^{14}$ and $R^{15}$, in each case together with atoms connecting them, form one or more rings, and $M^2$ is silicon, germanium or tin.

5. A compound of formula I

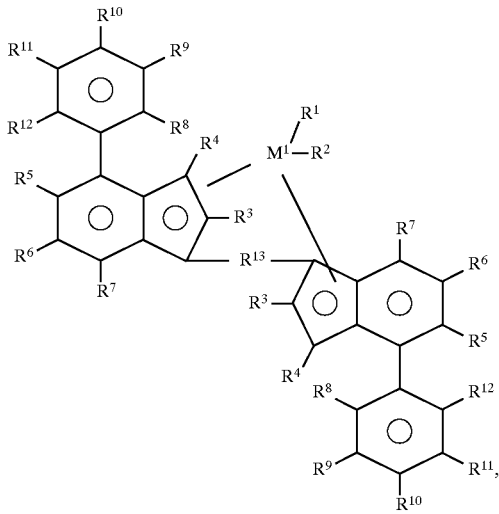

in which $M^1$ is a metal from group IVb, Vb or VIb of the Periodic Table, $R^1$ and $R^2$ are identical or different and are a hydrogen atom, a $C_1$–$C_{10}$-alkyl group, a $C_1$–$C_{10}$-alkoxy group a $C_8$–$C_{10}$-aryl group, a $C_8$–$C_{10}$-aryloxy group, a $C_2$–$C_{10}$-alkenyl group, a $C_7$–$C_{40}$-arylalkyl group, a $C_7$–$C_{40}$-alkylaryl group, a $C_8$–$C_{40}$-arylalkenyl group, an OH group or a halogen atom, the radicals $R^3$ are identical or different and are a hydrogen atom, a halogen atom, a $C_1$–$C_{10}$-alkyl group, which may be halogenated, a $C_8$–$C_{10}$-aryl group, an —$NR^{16}_2$, —$SR^{16}$, —$OSiR^{18}_3$, —$SiR^{16}_3$, or —$PR^{16}_2$ radical, in which $R^{18}$ is a halogen atom, a $C_1$–$C_{10}$-alkyl group or a $C_8$–$C_{10}$-aryl group, the radicals $R^{12}$ are identical or different and are a $C_1$–$C_{10}$-alkyl group, which may be halogenated, a $C_6$–$C_{10}$-aryl group, an —$NR^{16}_2$, —$SR^{16}$, —$OSiR^{16}_3$, —$SiR^{16}_3$ or —$PR^{16}_2$ radical, in which $R^{16}$ is a halogen atom, a $C_1$–$C_{10}$-alkyl group or a $C_8$–$C_{10}$-aryl group, $R^4$ to $R^{11}$ are identical or different and are as defined for $R^3$, or adjacent radicals $R^4$ to $R^{12}$, together with the atoms connecting them, form one or more aromatic or aliphatic rings, or the radicals $R^5$ and $R^8$ or $R^{12}$, together with the atoms connecting them, form an aromatic or aliphatic ring, $R^{13}$ is

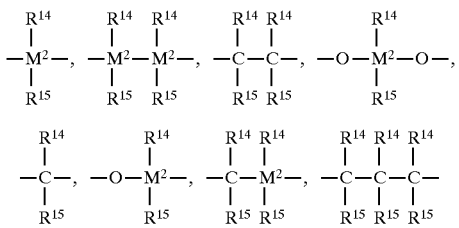

$=BR^{14}$, $=AlR^{14}$, —Ge—, —O—, —S—, $=SO$, $=SO_2$, $=NR^{14}$, $=CO$, $=PR^{14}$ or $=P(O)R^{14}$, where $R^{14}$ and $R^{15}$ are identical or different and are a hydrogen atom, a halogen atom, a $C_1$–$C_{10}$-alkyl group, a $C_1$–$C_{10}$-fluoroalkyl group, a $C_1$–$C_{10}$-alkoxy group, a $C_6$–$C_{10}$-aryl group, a $C_6$–$C_{10}$-fluoroaryl group, a $C_6$–$C_{10}$-aryloxy group, a $C_2$–$C_{10}$-alkenyl group, a $C_7$–$C_{40}$-arylalkyl group, a $C_7$–$C_{40}$-alkylaryl group or a $C_8$–$C_{40}$-arylalkenyl group, or $R^{14}$ and $R^{15}$, in each case together with atoms connecting them, form one or more rings, and $M^2$ is silicon, germanium or tin.

* * * * *